United States Patent [19]

Norbeck

[11] Patent Number: 5,420,276
[45] Date of Patent: May 30, 1995

[54] ANALOGS OF OXETANYL PURINES AND PYRIMIDINES

[75] Inventor: Daniel W. Norbeck, Lindenhurst, Ill.

[73] Assignee: Abbott Laboratories, Abbott Park, Ill.

[21] Appl. No.: 163,217

[22] Filed: Dec. 7, 1993

Related U.S. Application Data

[60] Division of Ser. No. 904,407, Jun. 25, 1992, which is a continuation-in-part of Ser. No. 615,138, Nov. 23, 1990, abandoned, which is a continuation-in-part of Ser. No. 574,617, Aug. 24, 1990, abandoned, which is a continuation-in-part of Ser. No. 453,520, Dec. 20, 1989, abandoned, which is a continuation-in-part of Ser. No. 116,605, Nov. 3, 1987, abandoned.

[51] Int. Cl.$^6$ .......................... C07D 405/04
[52] U.S. Cl. .................... 544/310; 549/475; 544/182; 546/268
[58] Field of Search .............. 544/310; 549/475

[56] References Cited

FOREIGN PATENT DOCUMENTS

| 182314 | 5/1986 | European Pat. Off. |
| 291917 | 11/1988 | European Pat. Off. |
| 334250 | 9/1989 | European Pat. Off. |
| 433898 | 6/1991 | European Pat. Off. |

OTHER PUBLICATIONS

Jerry March, Advanced Organic Chemistry, 3rd Edition, 1987, p. 975.
Carey et al, Advanced Organic Chemistry, Part B: Reactions and Synthesis, 2nd Edition, 1983 pp. 445–446.
Niitsuma, et al., Tet Lett. 28 4713 (1987).
Shimada, et al., J. of Antibiotics 12 1788 (1987).
Norbeck, et al., J. Am. Chem. Soc. 110 7217 (1988).

*Primary Examiner*—Cecilia Tsang
*Attorney, Agent, or Firm*—Steven R. Crowley

[57] ABSTRACT

A compound of the formula:

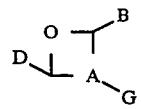

wherein B is a purin-9-yl group or a heterocyclic isostere of a purin-9-yl group; or a pyrimidin-1-yl group or a heterocyclic isostere of a pyrimidin-1-yl group; A is —CH— or A—G taken together is —C(=O)—, —C(=CH$_2$)—, —C(OH)(CH$_2$OH)— or

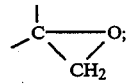

and G and D are functional groups; or a pharmaceutically acceptable salt or ester thereof.

6 Claims, No Drawings

ANALOGS OF OXETANYL PURINES AND PYRIMIDINES

This is a division of U.S. patent application Ser. No. 904,407, filed Jun. 25, 1992 allowed, which is a continuation-in-part of U.S. patent application Ser. No. 615,138, filed Nov. 23, 1990, which is a continuation-in-part of U.S. patent application Ser. No. 574,617, filed Aug. 24, 1990, which is a continuation-in-part of U.S. patent application Ser. No. 453,520, filed Dec. 20, 1989, which is a continuation-in-part of U.S. patent application Ser. No. 116,605, filed Nov. 3, 1987, all abandoned.

TECHNICAL FIELD

The present invention relates to novel compounds and compositions which have antiviral activity, processes for making such compounds, synthetic intermediates employed in these processes and a method for treating a human or other mammal in need of antiviral treatment.

BACKGROUND ART

Viruses are implicated in a variety of animal and human diseases. Numerous approaches have been proposed to combat these pathogens which include, but are not limited to, herpesviruses 1 and 2 (HSV-1 and HSV-2), influenza viruses A, B and C (orthomyxoviruses), parainfluenza viruses 1-4, mumps virus (paramyxovirus), adenoviruses, respiratory syncytial virus, Epstein-Barr virus, rhinoviruses, human immunodeficiency viruses (HIV), polioviruses, coxsackieviruses, echoviruses, rubella virus, varicella-zoster virus, neurodermotropic virus, variola virus, cytomegalovirus, hepatitis A, B and non-A, non-B viruses, papoviruses and rabies virus.

One approach in the development of antiviral compounds has been to identify compounds which interfere with the normal viral metabolism of nucleosides. Because the structures of these compounds are usually closely related to nucleosides which occur naturally in the mammalian host, few have good activity against the virus without untoward side effects. Some of the few compounds having activity are very expensive to produce. Thus, there is a continuing need for new compounds which act to kill viruses, to inhibit viral replication or to block the pathogenic actions of viruses.

DISCLOSURE OF THE INVENTION

In accordance with the present invention there are antiviral compounds of the formula:

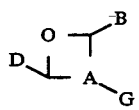

(I)

or a pharmaceutically acceptable salt or ester thereof.

B is a purin-9-yl group, a heterocyclic isostere of a purin-9-yl group, a pyrimidin-1-yl group or a heterocyclic isostere of a pyrimidin-1-yl group.

D is (i) hydrogen, (ii) $C_1$ to $C_{10}$ alkyl, (iii) —$CH_2OH$, (iv) —$CH_2OR_{20}$ wherein $R_{20}$ is $C_1$ to $C_6$ alkyl, (v) —$CH_2OC(O)R_{21}$ wherein $R_{21}$ is $C_1$ to $C_{10}$ alkyl, (vi) —$CH_2OC(O)CH(R_{22})(NHR_{23})$ wherein $R_{22}$ is the side chain of any of the naturally occuring amino acids and $R_{23}$ is hydrogen or —C(O)CH($R_{24}$)($NH_2$) wherein $R_{24}$ is the side chain of any of the naturally occuring amino acids, (vii) —$CH_2SH$, (viii) —$CH_2Cl$, (ix) —$CH_2F$, (x) —$CH_2Br$, (xi) —$CH_2I$, (xii) —C(O)H, (xiii) —$CH_2CN$, (xiv) —$CH_2N_3$, (xv) —$CH_2NR_{33}R_{34}$ wherein $R_{33}$ and $R_{34}$ are independently selected from hydrogen and $C_1$ to $C_{10}$ alkyl, (xvi) —$CO_2R_{35}$ wherein $R_{35}$ is hydrogen or $C_1$ to $C_{10}$ alkyl, (xvii) —$CH_2CH_2OH$, (xviii) —$CH_2CH_2OR_{20}$ wherein $R_{20}$ is as defined herein, (xix) —$CH_2CH_2OC(O)R_{21}$ wherein $R_{21}$ is as defined herein, (xx) —$CH_2CH_2OC(O)CH(R_{22})(NHR_{23})$ wherein $R_{22}$ and $R_{23}$ are as defined herein, (xxi) —$CH_2CH_2PO_3H_2$, (xxii) —$CH_2OPO_3H_2$, (xxiii) —$OCH_2PO_3H_2$ or (xxiv) —$CH_2CO_2R_{36}$ wherein $R_{36}$ is hydrogen, $C_1$ to $C_{10}$ alkyl, carboxyalkyl or aminoalkyl.

A is —CH— or A—G taken together is —C(=O)—, —C(=$CH_2$)—, —C(OH)($CH_2OH$)— or

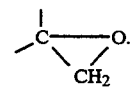

G is (i) hydrogen, (ii) $C_1$ to $C_{10}$ alkyl, (iii) —OH, (iv) alkoxy, (v) —$NH_2$, (vi) alkylamino, (vii) dialkylamino, (viii) —SH, (ix) thioalkoxy, (x) —$N_3$, (xi) —$CH_2OH$, (xii) —$CH_2OR_{25}$ wherein $R_{25}$ is $C_1$ to $C_6$ alkyl, (xiii) —$CH_2OC(O)R_{26}$ wherein $R_{26}$ is $C_1$ to $C_{10}$ alkyl, (xiv) —$CH_2OC(O)CH(R_{27})(NHR_{28})$ wherein $R_{27}$ is the side chain of any of the naturally occuring amino acids and $R_{28}$ is hydrogen or —C(O)CH($R_{29}$)($NH_2$) wherein $R_{29}$ is the side chain of any of the naturally occuring amino acids, (xv) —$CH_2SH$, (xvi) —$CH_2Cl$, (xvii) —$CH_2F$, (xviii) —$CH_2Br$, (xix) —$CH_2I$, (xx) —C(O)H, (xxi) —$CH_2CN$, (xxii) —$CH_2N_3$, (xxiii) —$CH_2NR_{30}R_{31}$ wherein $R_{30}$ and $R_{31}$ are independently selected from hydrogen and $C_1$ to $C_{10}$ alkyl, (xxiv) —$CO_2R_{37}$ wherein $R_{37}$ is hydrogen, $C_1$ to $C_{10}$ alkyl, carboxyalkyl or aminoalkyl, (xxv) —$CH_2CH_2OH$, (xxvi) —$CH_2CH_2OR_{25}$ wherein $R_{25}$ is independently as defined herein, (xxvii) —$CH_2CH_2OC(O)R_{26}$ wherein $R_{26}$ is independently as defined herein, (xxviii) —$CH_2CH_2OC(O)CH(R_{27})(NHR_{28})$ wherein $R_{27}$ and $R_{28}$ are independently as defined herein, (xxix) —$CH_2CH_2PO_3H_2$, (xxx) —$CH_2OPO_3H_2$, (xxxi) —$OCH_2PO_3H_2$ or (xxxii) —$CH_2CO_2R_{32}$ wherein $R_{32}$ is hydrogen, $C_1$ to $C_{10}$ alkyl, carboxyalkyl or aminoalkyl; with the proviso that when D is hydrogen or $C_1$ to $C_{10}$ alkyl then G is other than hydrogen or $C_1$ to $C_{10}$ alkyl.

Preferred compounds of the invention are compounds of the formula I wherein B is

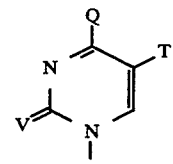

wherein
V is O or S;
Q is (i) —OH or (ii) —NH; and

T is (i) hydrogen, (ii) $C_1$ to $C_{10}$ alkyl, (iii) 2-haloethyl, (iv) halomethyl, (v) difluoromethyl, (vi) trifluoromethyl, (vii) halogen, (viii) vinyl, (ix) 2-halovinyl or (x) alkynyl;

A is CH and D and G are —$CH_2OH$; or a pharmaceutically acceptable salt or ester thereof.

The compounds of formula I contain two or more asymmetric carbon atoms and thus can exist as pure diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure. Appl. Chem. (1976) 45, 13–30.

The term "$C_1$ to $C_{10}$ alkyl" as used herein refers to straight or branched chain alkyl radicals containing from 1 to 10 carbon atoms including, but not limited to, methyl, ethyl, isopropyl, n-butyl, isobutyl, sec-butyl, n-pentyl, 1-methylbutyl, 2,3-dimethylbutyl, 2-methylpentyl, 2,2-dimethylpropyl, n-hexyl, n-heptyl, n-octyl, n-nonyl, n-decyl and the like.

The terms "alkoxy" and "thioalkoxy" as used herein refer to —$OR_{38}$ and —$SR_{38}$, respectively, wherein $R_{38}$ is a $C_1$ to $C_{10}$ alkyl group.

The term "carboxyalkyl" as used herein refers to a carboxylic acid group (—COOH) appended to a $C_1$ to $C_{10}$ alkyl radical.

The term "alkoxycarbonyl" as used herein refers to —$C(O) R_{39}$ wherein $R_{39}$ is an alkoxy group.

The term "aminoalkyl" as used herein refers to an amino group (—$NH_2$) appended to a $C_1$ to $C_{10}$ alkyl radical.

The term "alkynyl" as used herein refers to $C_2$ to $C_6$ straight or branched carbon chain which contains a carbon-carbon triple bond including, but not limited to, ethynyl, propynyl, butynyl and the like.

The term "halo" or "halogen" as used herein refers to Cl, Br, F or I.

The term "alkylamino" as used herein refers to —$NHR_{40}$ wherein $R_{40}$ is a $C_1$ to $C_{10}$ alkyl group.

The term "dialkylamino" as used herein refers to —$NR_{41}R_{42}$ wherein $R_{41}$ and $R_{42}$ are independently selected from $C_1$ to $C_{10}$ alkyl.

The term "side chain of any of the naturally occuring amino acids" as used herein refers to the functionality appended at the alpha carbon of any of the naturally occuring amino acids and includes, but is not limited to hydrogen (glycine), methyl (alanine), isopropyl (valine), hydroxymethyl (serine), benzyl (phenylalanine), and the like.

The term "N-protecting group" as used herein refers to those groups intended to protect nitrogen atoms against undesirable reactions during synthetic procedures and includes, but is not limited to, formyl, acetyl, pivaloyl, t-butylacetyl, trichloroethoxycarbonyl, t-butyloxycarbonyl (Boc), benzyloxycarbonyl (Cbz) or benzoyl groups or other nitrogen protecting groups known to those skilled in organic synthesis such as those disclosed in Greene, "Protective Groups in Organic Synthesis", pp. 218–287, (J. Wiley & Sons, 1981).

The term "hydroxy protecting group" or "O-protecting group" as used herein refers to those groups intended to protect a hydroxy group against undesirable reactions during synthetic procedures and includes, but is not limited to, substituted methyl ethers, for example, methoxymethyl, benzyloxymethyl, 2-methoxyethoxymethyl, 2-(trimethylsilyl)ethoxymethyl and tetrahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; acyl groups such as acetyl and benzoyl; sulfonates such as mesylate and tosylate; or other hydroxy protecting groups known to those skilled in organic synthesis such as those disclosed in Greene, "Protective Groups in Organic Synthesis", pp 10–71, (J. Wiley & Sons, 1981).

The term "heterocyclic isostere of a purin-9-yl group" as used herein refers to a heterocyclic group which has a similar structure and similar properties when compared to a purin-9-yl group. In addition, the isostere may contain different atoms and not necessarily the same number of atoms as long as the isostere possesses the same total or valence electrons in the same arrangement as does a purin-9-yl group. For example, well known isosteric pairs of molecules include the pair carbon monoxide and atmospheric nitrogen and the pair cyanide ion and acetylide ion. Heterocyclic isosteres of a purin-9-yl group include, but are not limited to, compounds of the formula:

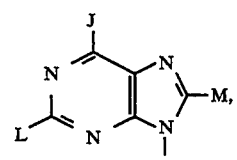

1)

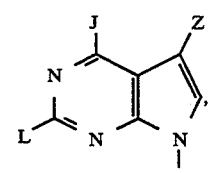

2)

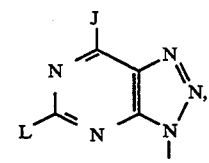

3)

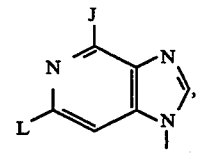

4)

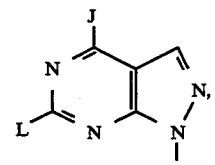

5)

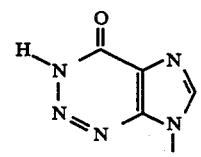

6)

and

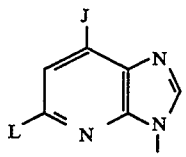

wherein J and L are independently selected from (i) hydrogen, (ii) —OH, (iii) halogen, (iv) alkoxy, (v) —SH, (vi) thioalkoxy, (vii) —N$_3$, (viii)

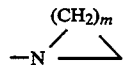

wherein m is 1 to 5, (ix) —NR$_1$R$_2$ wherein R$_1$ and R$_2$ are independently selected from hydrogen and C$_1$ to C$_{10}$ alkyl, (x) —NHC(O)R$_3$ wherein R$_3$ is hydrogen, C$_1$ to C$_{10}$ alkyl, carboxyalkyl or aminoalkyl, (xi) —N=CHNR$_4$R$_5$ wherein R$_4$ and R$_5$ are independently selected from C$_1$ to C$_{10}$ alkyl, (xii) —N(R$_6$)OR$_7$ wherein R$_6$ and R$_7$ are independently selected from hydrogen and C$_1$ to C$_{10}$ alkyl, and (xiii) —N(R$_8$)NR$_9$R$_{10}$ wherein R$_8$, R$_9$ and R$_{10}$ are independently selected from hydrogen and C$_1$ to C$_{10}$ alkyl; M is (i) C$_1$ to C$_{10}$ alkyl, (ii) halogen, (iii)

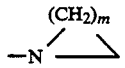

wherein m is 1 to 5, or (iv) —NR$_1$R$_2$ wherein R$_1$ and R$_2$ are as defined above; and Z is (i) hydrogen, (ii) halogen, (iii) formyl, (iv) carboxyl, (v) alkoxycarbonyl or (vi) cyano.

The term "heterocyclic isostere of a pyrimidin-1-yl group" as used herein refers to a heterocyclic group which has a similar structure and similar properties when compared to a pyrimidin-1-yl group. In addition, the isostere may contain different atoms and not necessarily the same number of atoms as long as the isostere possesses the same total or valence electrons in the same arrangement as does a pyrimidin-1-yl group. For example, well known isosteric pairs of molecules include the pair carbon monoxide and atmospheric nitrogen and the pair cyanide ion and acetylide ion. Heterocyclic isosteres of a pyrimidin-1-yl group include, but are not limited to, compounds of the formula:

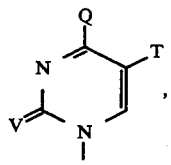 1)

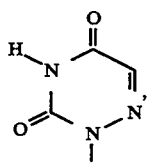 2)

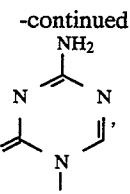 3)

and

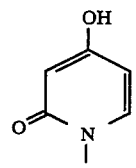 4)

wherein
V is O or S;
Q is (i) —OH, (ii) —SH, (iii) alkoxy, (iv) thioalkoxy, (v) halogen, (vi)

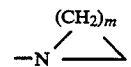

wherein m is 1 to 5, (vii) —NR$_1$R$_2$ wherein R$_1$ and R$_2$ are independently as defined herein or (viii) —NHC(O)R$_3$ wherein R$_3$ is independently as defined herein;

and T is (i) hydrogen, (ii) C$_1$ to C$_{10}$ alkyl, (iii) 2-haloethyl, (iv) halomethyl, (v) difluoromethyl, (vi) trifluoromethyl, (vii) halogen, (viii) cyano, (ix) nitro, (x) vinyl, (xi) 2-halovinyl, (xii) alkynyl, (xiii) hydroxmethyl, (xiv) formyl, (xv) azidomethyl, (xvi) 2-hydroxyethyl, (xvii) —NR$_1$R$_2$ wherein R$_1$ and R$_2$ are independently as defined herein, (xviii) —NHOH, (xix) —SH, (xx) propenyl, (xxi) 3,3,3-trifluoropropenyl, (xxii) 2-(alkoxycarbonyl)ethenyl, (xxiii) 2-cyanoethenyl, (xxiv)

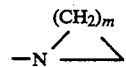

wherein m is 1 to 5, or (xxv) —CH$_2$NR$_1$R$_2$ wherein R$_1$ and R$_2$ are independently as defined herein.

The compounds of the present invention can be prepared by various methods, including those disclosed in Schemes 1–4.

As shown in Scheme 1, treatment of 1, wherein B is as defined herein, with a suitable alkyl halide, arylalkyl halide (e.g., triphenylmethyl chloride), aroyl halide, alkanoyl halide, or silyl halide (e.g., trimethylsilyl chloride) in a polar solvent such as N,N-dimethylformamide (DMF), tetrahydrofuran (THF), CH$_2$Cl$_2$ or pyridine at a temperature of from about 0° to about 60° C. affords the protected derivative 2 (R* is an O-protecting group). Preferably, 1 is treated with t-butylchlorodimethylsilane in pyridine at room temperature for about 24 hours to obtain 2 (R*=(t-Bu)(Me)$_2$Si—).

When the substituent B in 1 or 2 is a purine having a 6-amino substituent, the 6-amino substituent can be protected by acylation with an alkanoyl chloride (e.g., acetyl chloride and the like) or aroyl chloride (e.g., benzoyl chloride or p-nitrobenzoyl chloride or the like) or a corresponding anhydride such as acetic anhydride in a solvent such as pyridine. Subsequent treatment with a dilute aqueous base such as sodium carbonate, potassium carbonate, potassium hydroxide or preferably 1M aqueous sodium hydroxide at a temperature of from about $-20°$ to about $40°$ C., preferably at about $0°$ C., affords diprotected 2. In the preferred case, the benzoyl group is used to protect the 6-amino group. The two protecting groups can also be introduced in the reverse order of that described above.

The free hydroxyl group in 2 is converted to an activated ester leaving group by treatment with a sulfonyl chloride (e.g., p-toluenesulfonyl chloride or trifluoromethanesulfonyl chloride and the like) or sulfonic acid anhydride (e.g., methanesulfonic acid anhydride) in a solvent such as pyridine or dichloromethane, optionally containing a base such as triethylamine, at a temperature of from about $-10°$ to about $40°$ C. for a period of from about 1 hour to about 24 hours. In a preferred method, 2 is treated with methanesulfonyl chloride in pyridine at $0°$ C. for 2 hours to provide 3 ($R^{**}=-SO_2Me$). The leaving group in 3 is then displaced with an appropriate nucleophile (NuH) in a polar solvent such as acetone, 2-butanone, THF, DMF or dimethoxyethane (DME) to furnish 4. Suitable nucleophilic reagents include $LiN_3$, $NaN_3$, n-$Bu_4NN_3$, KF, CsF, n-$Bu_4NF$, LiBr, NaBr, n-$Bu_4NBr$, LiI, NaI, n-$Bu_4NI$, LiCl, n-$Bu_4NCl$, $CH_3CH_2NH_2$, $CH_3NH_2$ and lithium triethylborohydride. The compounds 4 thus obtained are converted to the compounds of this invention (I) by removal of the hydroxyl protecting group. In the preferred case in which B is 6-benzamidopurin-9-yl and $R^*$ is (t-Bu)(Me)$_2$Si—, the deprotection is accomplished with a source of fluoride ion such as KF, CsF or preferably n-$Bu_4NNF$ in a polar solvent such as DMF, $CH_3CN$ or preferably THF at a temperature of about $25°$ C. In the case in which a nitrogen protecting group has been employed, this group must also be removed. In the preferred case in which the nitrogen protecting group is benzoyl, treatment of 4 with dilute aqueous sodium hydroxide in methanol or sodium ethoxide in ethanol provides I.

An alternative preparation of 1 (Nu=F) involves direct treatment of the alcohol 2 with a fluorinating agent such as diethylaminosulfurtrifluoride (DAST) in a nonhydroxylic solvent such as dichloromethane at a temperature between $-78°$ and $25°$ C., preferably about $-40°$ C. The amino derivative 4 (Nu=—$NH_2$) is obtained by reduction of the corresponding azide (4, Nu=—$N_3$), preferably employing hydrogen and a palladium catalyst. These analogs 4 are converted to compounds of this invention as described above.

Compounds of formula I wherein B is a 6-alkylaminopurin-9-yl group or a 6-amidopurin-9-yl group can be synthesized according to the route outlined in Scheme 2. For example, treatment of 1a with sodium nitrite in acetic acid or an acetate buffer at a temperature of about $-10°$ to $60°$ C. affords the deaminated material 6. Suitable conditions include the use of amyl nitrite in 50% acetic acid. Alternatively, this transformation can be accomplished enzymatically. The hydroxymethyl substituents on the oxetane ring of 5 are protected using an acylating agent such as nitrobenzoyl chloride or benzoylchloride in a solvent such as pyridine or DMF at a temperature of about $-10°$ to $60°$ C. In the preferred method, 5 is treated with trifluoroacetic anhydride in $CH_2Cl_2$ at $0°$ to $20°$ C. to obtain the diacyl derivative 6. Treatment of 6 with DMF/thionyl chloride in dichloromethane, preferably at reflux temperature followed by cleavage of the acyl protecting groups, preferably using methanol and neutral alumina provides 7. Exposure of 7 to an amine ($R_aR_bNH$, wherein $R_a$ and $R_b$ are independently selected from $C_1-C_{10}$ alkyl and hydrogen), at a temperature of from about $25°$ C. to about $200°$ C. furnishes 8. A preferred method involves the reaction of 7 with methylamine at about $100°$ C. to afford 8. Compound 1 in Scheme 1 may be replaced with the compounds 8 of Scheme 2 to obtain the corresponding N-6 substituted derivatives I.

The compounds of the invention of the formula I can be prepared as shown in Scheme 3, where "P" is a hydroxyl protecting group intended to protect against undersirable side reactions during synthetic procedures. "P" includes, but is not limited to, t-butyldimethylsilyl, t-butyldiphenylsilyl, triphenylmethyl, benzoyl, acetyl and the like. "B" is as defined above.

The process shown in the scheme entails ring contraction of a 3-deoxy nucleoside 11 to an oxetane ring via rearrangement of the diazoketone 12.

Scheme 4 shows the process outlined in Scheme 3 wherein B is thymine, cytosine or uracil. P' and P" are hydroxyl protecting groups intended to protect against undesirable side reactions during synthetic procedures. P' and P" are independently selected from hydroxyl protecting groups including, but not limited to, t-butyldimethylsilyl, triphenylmethyl, benzoyl, p-chlorobenzoyl, acetyl, benzyl and the like.

The process shown in Scheme 4 entails ring contraction of a 2',3'-dideoxy-2'-oxo nucleoside 11 (wherein the hydroxyl protecting group P' is preferably t-butlydimethylsilyl) to an oxetane ring via rearrangement of the diazoketone 12, followed by reduction of the ester 13 (R" is loweralkyl, for example, $CH_3$) to the 2'-hydroxymethyl compound 14 and removal of the hydroxyl protecting group to give I.

In the case where B is uracil, the epoxide 15 (wherein the 5'-hydroxyl protecting group P' is preferably a benzoyl group) is opened to compound 16 by treatment with an iodide salt such as sodium iodide in the presence of an acid in a polar solvent such as 2-butanone. The iodo derivative 16 is reduced to 10 preferably with tri-n-butyl tin hydride and the 5'-hydroxyl group deprotected, for example by treatment with potassium carbonate in methanol solution. The 5'-hydroxyl group is deprotected, preferably with a t-butyldimethylsilyl group and the 2'-hydroxyl group is oxidized to the ketone to afford compound 11, for example by treatment with chromium trioxide-pyridine reagent.

In the case where B is thymine, 3'deoxy-5-methyluridine with both sugar hydroxyls protected (compound 17, P' and P" are O-protecting groups), preferably as p-chlorobenzoyl esters, is deprotected in basic solution, for example using sodium methoxide in methanol solution. The 5'-hydroxyl group is selectively reprotected (P'), preferably as the t-butyldimethylsilyl (TBS) derivative and the 2'-hydroxyl group is oxidized by treatment with oxidizing agent such as chromium trioxide-pyridine reagent to afford 11.

In the case where B is cytosine, cytosine with the 4-amino group protected as the N-acetyl derivative is treated with hexamethyldisilazane to give 18. Compound 18 is coupled in the presence of tin tetrachloride with 1-O-acetyl-3-deoxyribose, preferably with the 2'- and 5'-hydroxyl groups protected (P' and P" are O-protecting groups) as p-chlorobenzoyl esters (20) to give compound 19. The protecting groups are then removed from the 2'- and 5'-hydroxyl groups, for example by treatment with ammonium hydroxide in methanol solution, and the 5'-hydroxyl group selectively reprotected, preferably by treatment with t-butyldimethylsilyl chloride. The 4-amino group is reprotected, preferably as the N,N-dimethylaminomethylene derivative, and the 2'-hydroxyl group is then oxidized, for example with DMSO in the presence of oxalyl chloride, to afford 11.

Scheme 5a shows the conversion of protected diol 14 to the monohydroxy compound 21. Oxidation (for example, with Dess-Martin periodinane) of 14 to aldehyde 19, followed by deformylation (for example, with tris(triphenylphosphine)rhodium (I)), provides 20. Deprotection then gives 21.

Scheme 5b shows the preparation of triol 24 and diol 25. Compound 22 wherein L is a leaving group (for example, mesylate) is treated with a base (for example, DBU) to provide olefin 23. Oxidation (for example with N-methylmorpholine-N-oxide/OsO4), followed by deprotection, provides triol 24. Oxidation of 24 (for example, with sodium periodate), followed by reduction (for example, with sodium borohydride), gives the diol 25.

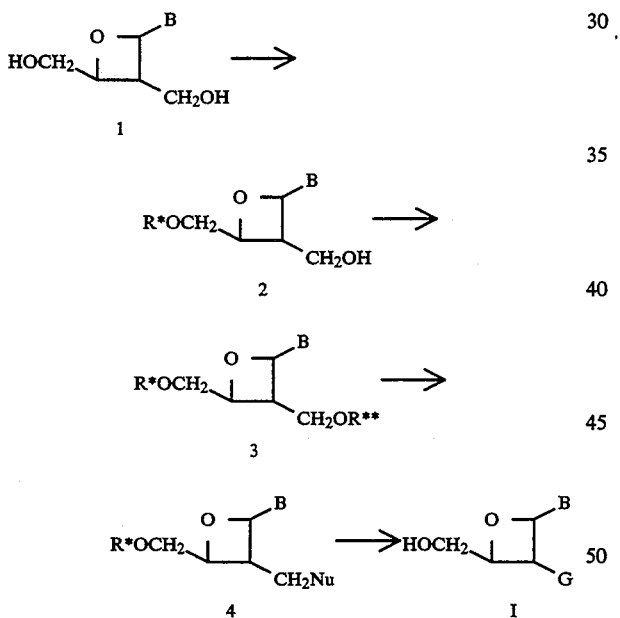

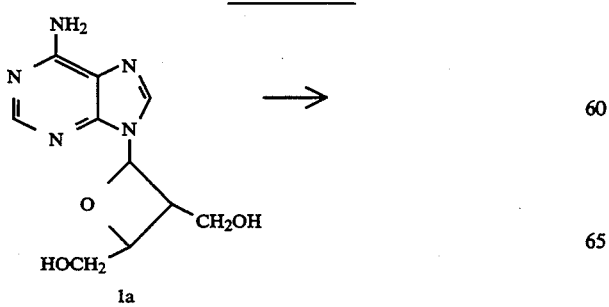

-continued
SCHEME 2

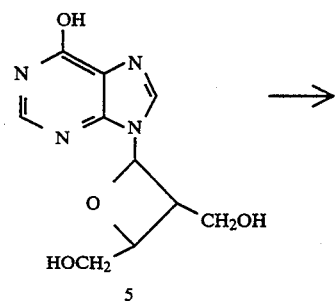

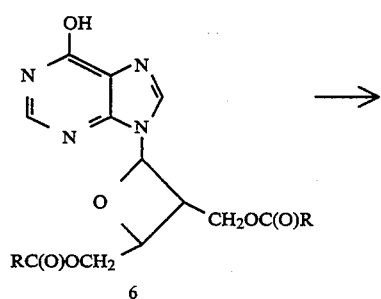

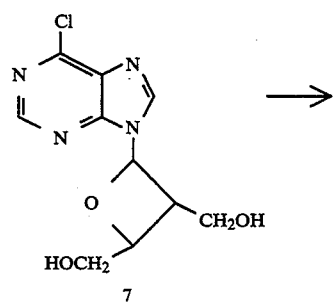

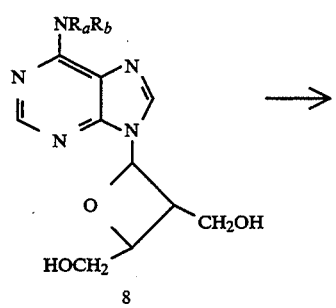

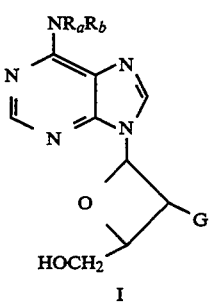

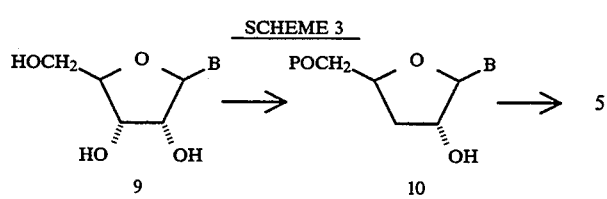
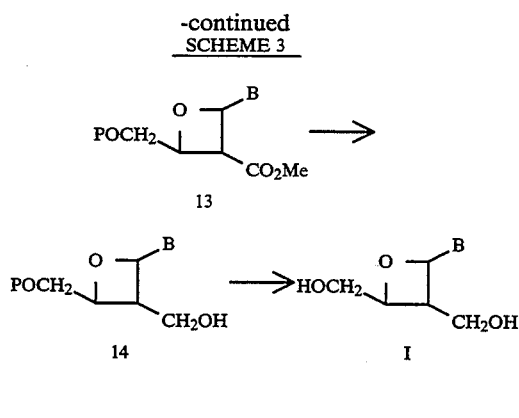
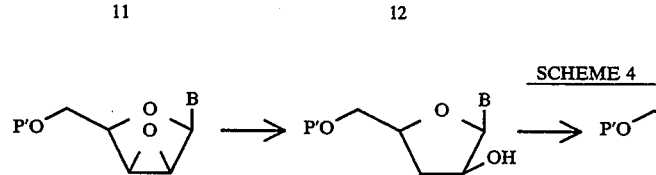
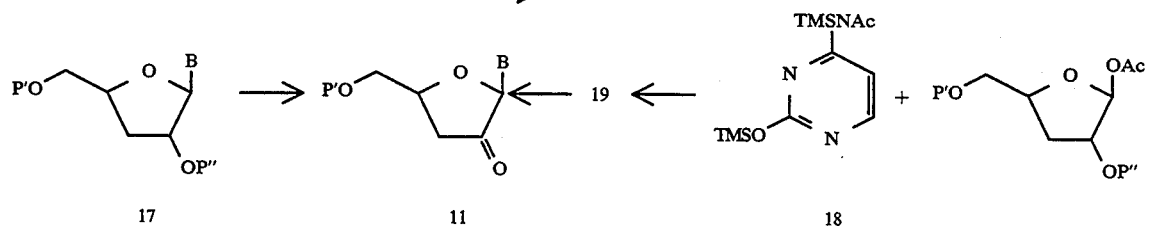
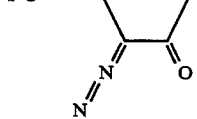
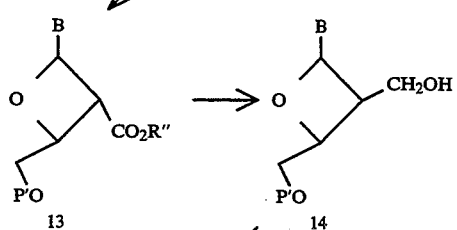
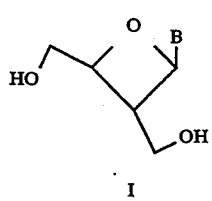

SCHEME 5

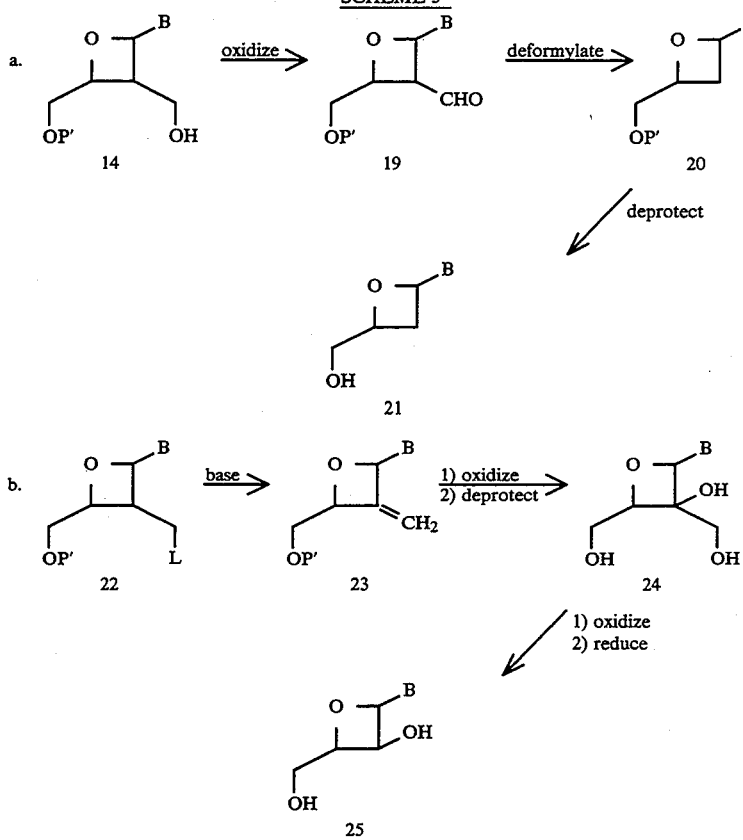

The foregoing may be better understood from the following examples, which are presented for purposes of illustration and are not intended to limit the scope of the inventive concepts. As used in the following examples, the references to compounds, such as (1), (2), (3), etc., and to substituents, such as R, $R_a$, $R_b$, etc., refer to the corresponding compounds and substituents in the foregoing reaction schemes and formulae.

The following examples will serve to further illustrate preparation of the novel compounds of the invention.

Example 1

9-((2R,3R,4S)-4-Hydroxymethyl-3-methyl-oxetan-2-yl)adenine (a) In a round-bottom flask were placed 10 g of 9-((2R, 3R, 4S)-3,4-bis-hyroxymethyl-oxetan-2-yl)-adenine and 100 mL of pyridine. To the system was added 6.4 g of tert-butylchlorodimethylsilane, and the reaction mixture was stirred under nitrogen at room temperature for 1 day. The mixture was diluted with ethyl acetate and washed with saturated aqueous sodium bicarbonate and brine, dried (sodium sulfate) and concentrated with a rotary evaporator. The residue was purified by column chromatography to afford 9-((2R,3R,4S)-4-t-butyldimethylsiloxymethyl-3-hydroxymethyl-oxetan-2-yl)adenine.

(b) Under a nitrogen atmosphere, in a round-bottom flask were placed 1.8 g of the product of (a) and 8 mL of dichloromethane. To this stirring solution, at 0° C., were added 1.1 g of triethylamine and 0.69 g of methanesulfonyl chloride. The cold bath was removed, and the reaction mixture was stirred at room temperature for approximately 2 h. The reaction mixture was diluted with ethyl acetate, washed with saturated aqueous sodium bicarbonate and brine and dried over sodium sulfate. The solvent was removed with a rotary evaporator to afford 9-((2R,3R,4S)-4-t-butyldimethylsiloxymethyl-3-methanesulfonyloxymethyl-oxetan-2-yl)adenine.

(c) Under a nitrogen atmosphere, in a roundbottom flask were placed 0.44 g of the compound of (b) and 0.5 mL of THF. To this stirring solution, at 0° C., was added 1.2 mL of 1M lithium triethylborohydride in THF. The cold bath was removed, and the reaction mixture was stirred at room temperature for 4 h. The mixture was partitioned between ethyl acetate and saturated aqueous sodium bicarbonate. The layers were separated, and the organic phase was washed with brine, dried ($Na_2SO_4$) and concentrated with a rotary evaporator. The residue was purified by column chromatography to afford 9-((2R, 3R, 4S)-4-t-butyldimethylsiloxymethyl-3-methyl-oxetan-2-yl)adenine.

(d) Under a nitrogen atmosphere, in a round-bottom flask was placed 0.35 g of the compound of (c). To the system was added 1.4 mL of 1M n-Bu4NF in THF. The reaction mixture was stirred at room temperature for 6 h and concentrated with a rotary evaporator. The residue was triturated with aqueous methanol and the resulting solid I ($X=CH_3$, $R_a=R_b=H$) was collected by suction filtration, rinsed with ice cold methanol and ether and dried under vacuum.

Example 2

9-((2R,3R,4S)-3-Fluoromethyl-4-hydroxymethyl-oxetan-2-yl)adenine

The procedures of Examples 1(a) and 1(b) can be repeated to obtain 9-((2R,3R,4S)-4-t-butyldimethylsiloxymethyl-3-methanesulfonyloxymethyl-oxetan-2-yl)adenine.

Under a nitrogen atmosphere, in a round-bottom flask was placed 0.44 g of the foregoing compound. To the system was added 8 mL of 1M n-Bu$_4$NF, and the reaction mixture was heated at reflux for 4 h. The mixture was cooled to room temperature and concentrated with a rotary evaporator. Trituration of the resulting viscous oil with MeOH—H$_2$O afforded a white solid which was collected by suction filtration, rinsed with ice-cold methanol and ether and dried under vacuum.

Example 3

9-((2R,3R,4S)-3-Iodomethyl-4-hydroxymethyl-oxetan-2-yl)adenine (a) The procedure of Example 2 can be repeated, replacing n-Bu$_4$NF with n-Bu$_4$NI, to obtain 4 (Nu=I, R=—Si(t-Bu)(Me)$_2$).

(b) The procedure of Example 1(d) can be repeated replacing 9-((2R,3R,4S)-4-t-butyldimethylsiloxymethyl-3-methyl-oxetan-2-yl)adenine with the material obtain the desired compound. Example 3(a) to obtain the desired compound.

Example 4

9-((2R,3R,4S)-3-Azidomethyl-4-hydroxymethyl-oxetan-2-yl)adenine

The procedure of Example 3 can be repeated, replacing n-Bu$_4$NI with n-Bu$_4$NN$_3$ to obtain the desired compound.

Example 5

9-((2R,3R,4S)-3-Aminomethyl-4-hydroxymethyl-oxetan-2-yl)adenine (a) The procedure of Example 4 can be repeated to obtain I (X=—CH$_2$N$_3$, R$_a$=R$_b$=H).

(b) In a round-bottom flask were placed 0.28 g of the compound of (a) and 10 mL of methanol. To the system (flushed with nitrogen) was added 0.2 g of 5% palladium on carbon. The system was placed under an atmosphere of H$_2$, and the mixture was stirred at room temperature for 1 h. The catalyst was removed by suction filtration through a pad of celite and rinsed well with methanol. The filtrate was concentrated with a rotary evaporator to afford the desired compound.

Example 6

9-((2R,3R,4S)-3-Chloromethyl-4-hydroxymethyl-oxetan-2-yl)adenine

The procedure of Example 3 can be repeated, replacing n-Bu$_4$NI with LiCl and THF with 2-butanone to afford the title compound.

Example 7

9-((2R,3R,4S)-4-Hydroxymethyl-3-methoxymethyl-oxetan-2-yl)adenine (a) Under a nitrogen atmosphere, in a round-bottom flask were placed 2.5 g of 9-((2R,3R,4S)-3,4-bis-hyroxymethyl-oxetan-2-yl)adenine and 40 mL of pyridine. To the system, at 0° C., was added 4.6 g of benzoyl chloride, the cold bath was removed, and the reaction mixture was stirred at room temperature for 1 day. The reaction mixture was diluted with a small amount of acetone and poured into ice/water. The resulting precipitate was collected by suction filtration and treated with 20 mL of 1M aqueous sodium hydroxide in 40 mL of DMF. The reaction mixture was diluted with saturated aqueous sodium bicarbonate and extracted with several portions of chloroform. The chloroform extracts were dried (Na$_2$SO$_4$) and concentrated with a rotary evaporator, and the crude product was rinsed with ether and recrystallized from ethanol-water to obtain 6-benzamido-9-((2R,3R,4S) 3,4-bis(hydroxymethyl)-oxetan-2-yl)purine.

(b) Under a nitrogen atmosphere, in a round-bottom flask were placed 2.8 g of the compound obtained in (a) and 15 mL of pyridine. To the system was added 2.8 g of trityl chloride, and the reaction mixture was stirred at room temperature for 5 days. The reaction mixture was partitioned between ethyl acetate and saturated aqueous sodium bicarbonate, and the layers were separated. The ethyl acetate solution was washed with brine, dried over sodium sulfate and the solvent was removed with a rotary evaporator to afford a white solid. The crude material was subjected to column chromatography to obtain 6-benzamido-9-((2R,3R,4S)4-hydroxymethyl-3-triphenylmethoxymethyl-oxetan-2-yl)purine.

(c) Under a nitrogen atmosphere, in a round-bottom flask were placed 0.6 g of the compound from (b) and 1 mL of DMF. To the system was added 80 mg of solid NaOH and 0.15 g of iodomethane. The reaction mixture was stirred at room temperature for 1 day. The reaction mixture was diluted with chloroform and washed with saturated aqueous sodium bicarbonate and brine, dried (sodium sulfate) and concentrated with a rotary evaporator. The crude product was rinsed with hexanes to afford 6-benzamido-9-((2R,3R,4S)-4-methoxymethyl-3-triphenylmethoxymethyl-oxetan-2-yl)purine.

(d) In a round-bottom flask were placed 0.4 g of the foregoing compound and 2 mL of ethanol. The system was flushed with nitrogen. To the system was added 0.2 g of 10% Pd on carbon, and the system was placed under an atmosphere of hydrogen. The reaction mixture was stirred at room temperature for 14 h, and the catalyst was removed by suction filtration through a pad of celite. To the system was added 2 mL of a solution prepared by dissolving 60 mg of sodium in 10 mL of ethanol, and the reaction mixture was heated at reflux for 3 h. The reaction mixture was concentrated with a rotary evaporator, water was added to the system and the solution was brought to pH 7 with acetic acid. This solution was washed with three portions of ethyl acetate, and the aqueous solution was concentrated with a rotary evaporator. The residue was recrystallized from water to afford the pure title compound.

Example 8

9-((2R,3R,4S)-4-Hydroxymethyl-3-thiomethyl-oxetan-2-yl)adenine (a) The procedures of Examples 1(a) and 1(b) can be repeated to obtain 9-((2R,3R,4S)-4-t-butyl-dimethylsiloxymethyl-3-methanesulfonyloxymethyloxetan-2-yl)adenine.

(b) Under an argon atmosphere, in a round-bottom flask were placed 0.75 g of sodium and 26 mL of ethanol. To this resulting solution of sodium ethoxide was added dropwise 3.83 mL of phenylmethanethiol. In a separate flask, under argon, were placed 0.84 of the compound from (a) and 2 mL of ethanol. To this stirring solution was added 2 mL of the mercaptide solution prepared above, and the reaction mixture was stirred at room temperature for 1 day. The resulting solid precipitate ($C_7H_7SO_3Na$) was removed by suction filtration through a celite pad. The filtrate was concentrated with a rotary evaporator, and the residue was partitioned between water and chloroform. The layers were separated, and the aqueous phase was extracted with two portions of chloroform. The combined chloroform extracts were washed with 1M aqueous sodium hydroxide and brine, dried (Na) and concentrated with a rotary evaporator. The crude product was purified by column chromatography to afford 9-((2R,3R,4S)-3-benzylthiomethyl-4-t-butyldimethylsiloxymethyl-oxetan-2-yl)adenine.

(c) Under an argon atmosphere, into a 3-neck round-bottom flask equipped with a dry-ice condenser and a gas inlet adapter was distilled approximately 25 mL of ammonia. To the system was added 0.85 of the compound of (b) followed by 170 mg of sodium (in several small portions), and the blue solution was stirred at −78° C. for 2 h. To the system was cautiously added 300 mg of ammonium chloride, and the cold bath was removed. After the ammonia evaporated, the resulting solid was rinsed with ether. The residue was dissolved in water and brought to pH 7 with acetic acid. This solution was extracted with several portions of chloroform. The chloroform extracts were dried over sodium sulfate, and the solvent was removed with a rotary evaporator to afford crude 9-((2R,3R,4S)-4-t-butyldimethylsiloxy-methyl-3-thiomethyl-oxetan-2-yl)adenine.

(d) The procedure of Example 1 (d) is then performed using the product of (c) as a starting material, to obtain the title compound.

Example 9

6-Methylamino-9-((2R,3R,4S)-3,4-bis(hydroxymethyl)-oxetan-2-yl)purine (a) To a suspension of 2.0 g of 1 in 110 mL of 0.02M aqueous $KH_2PO_4$ buffer solution was added 20 mg of Type II adenosine deaminase. The reaction mixture was stirred at room temperature for 1 day and concentrated to a volume of 80 mL. The resulting suspension was filtered and the filtrate was concentrated to approximately 20 mL. The resulting suspension was filtered. The filtrate was diluted with 20 mL of ethanol and concentrated to a volume of less than 50 mL. This mixture was also filtered. The combined solids were suspended in approximately 80 mL of hot 80% ethanol. This mixture was filtered, and the filtrate was cooled at 0° C. for 1 day. The resulting 9-((2R,3R,4S)-3,4-bis(hydroxymethyl)-oxetan-2-yl)hypoxanthine was collected by suction filtration. Alternatively, this transformation can be accomplished nonenzymatically, employing amyl nitrate in 50% acetic acid.

(b) Under a nitrogen atmosphere, in a round-bottom flask were placed 1.0 g of the compound of (a) and 20 mL of dichloromethane, and the system was cooled in an ice bath. To the system was added 9.0 g of trifluoroacetic anhydride, and the reaction mixture was stirred for 2 h and concentrated with a rotary evaporator. The residue was subjected to high vacuum for 1 h to afford 9-((2R,3R,4S)-3,4-bis(trifluoroacetoxymethyl)-oxetan-2-yl)hypoxanthine.

(c) Under a nitrogen atmosphere, in a 3-neck round-bottom flask equipped with a reflux condenser and a pressure-equalizing addition funnel were placed the product obtained above and 100 mL of dichloromethane. To this stirring mixture was added dropwise a solution of 3.2 mL of thionyl chloride and 1.6 mL of DMF in 40 mL of dichloromethane. During this addition, the mixture was heated to maintain a gentle reflux. The reaction mixture was heated at reflux for a total period of 8 h and cooled to room temperature. The reaction mixture was cooled to 0° C. and a small amount of solid was removed by suction filtration. The filtrate was poured slowly into a cold 1M aqueous solution of sodium bicarbonate with vigorous stirring. The layers were separated, and the aqueous phase was extracted with dichloromethane. The combined organic fractions were dried ($Na_2SO_4$), and the solvent was removed with a rotary evaporator. The crude material was subjected to column chromatography on neutral alumina using methanol as the eluant to obtain 6-chloro-9-((2R,3R,4S)-3,4-bis(hydroxymethyl)-oxetan-2-yl)purine.

(d) In a sealed tube were placed 0.54 g of the foregoing compound in 30 mL of methanol containing 8 g of methylamine. The mixture was heated at 100° C. for 12 h. The reaction mixture was cooled to room temperature and concentrated with a rotary evaporator. The residue was dissolved in water and extracted with ether. The aqueous phase was brought to pH 7 with acetic acid and sodium bicarbonate and concentrated. The residue was recrystallized from a small amount of water. The solid was collected and rinsed with ice-cold water, methanol and ether to afford the pure title compound.

Example 10

6-Methylamino-9-(2R,3R,4S)-3-fluoromethyl-4-hydroxymethyl-oxetan-2-yl)purine

The procedure of Example 9 can be repeated replacing the starting compound of Example 9 (a) with the product of Example 2 to obtain the title compound.

Example 11

6-Methylamino-9-((2R,3R,4S)-4-hydroxymethyl-3-methyl-oxetan-2-yl)purine

The procedure of Example 9 can be repeated replacing the starting compound of Example 9 (a) with the product of Example 1 to obtain the desired compound.

Example 12

6-Methylamino-9-((2R,3R,4S)-3-azido-4-hydroxymethyl-oxetan-2-yl)purine

The procedure of Example 9 can be repeated replacing the starting compound of Example 9(a) with the product of Example 4 to obtain the title compound.

Example 13

5'-O-(t-Butyldimethylsilyl)-3'-deoxyadenosine

To a stirred solution of 9.5 g (38.1 mmol) of 2',3'-anhydroadenosine (Robins, M. J.; Hansske, F; Low, N. H.; Park, J. I. Tetrahedron Lett. 1984, 367–370) in 114 mL of pyridine was added 11.5 g (76.2 mmol) of t-butyldimethylsilyl chloride. After 3.5 h at room temperature, an additional 5.75 g (38.1 mmol) of t-butyldimethylsilyl chloride was added. After a total of 4.25 h, the reaction mixture was diluted into 2 L of water and extracted with 3×500 mL of dichloromethane. The combined dichloromethane extracts were washed with one liter of saturated aqueous sodium bicarbonate, with 3×500 mL of water, and then dried over magnesium sulfate. Concentration under reduced pressure afforded 13.3 g of 5'-O-(t-butyldimethylsilyl)-2',3'-anhydroadenosine. To a stirred solution of 2.0 g (5.50 mmol) of 5'-O-(t-butyldimethylsilyl)-2',3'-anhydroadenosine in 55 mL of THF at 0° C. was added 22 mL (22 mmol) of a 1M solution of lithium triethyl borohydride in THF. The reaction mixture was then allowed to warm to room temperature. After 3 hours, the reaction mixture was recooled to 0° C. and then carefully treated with 4.0 mL of 5% aqueous acetic acid. The resulting mixture was diluted with 150 mL of EtOAc, washed with 3×100 mL of saturated aqueous NaCl, dried over magnesium sulfate, concentrated under reduced pressure, and then coevaporated with three portions of chloroform. Chromatography of the residue on silica gel with a 100:0 to 97:3 chloroform/methanol gradient afforded 1.8 g (90%) of the title compound: colorless glass; $R_f$=0.10 (silica gel 60 F-254, 0.25 mm, E. Merck (SG), 95:5 CHCl$_3$:MeOH); $[\alpha]_D^{23}$ −47.8° (c 2.47, CHCl$_3$); IR (CDCl$_3$) 3480, 3415, 3320, 3165, 3125, 2960, 2935, 2860, 1635, 1595, 1575, 1470, 1415, 1330, 1290, 1255, 1210, 1135, 1090, 995 cm$^{-1}$; $^1$H NMR (300 MHz, CDCl$_3$, TMS=0.00 ppm) δ0.08, 0.09 (2s, 6H, (CH$_3$)$_2$Si), 0.88 (s, 9H, (CH$_3$)$_3$CSi), 2.10 (ddd, 1H, J=13.5 Hz, J'=6.5 Hz, J''=4.0 Hz, 3'-H), 2.34 (ddd, 1H, J=13.5 Hz, J'=7.5 Hz, J''=6.0 Hz, 3'-H), 3.74 (dd, 1H, J=12.0 Hz, J'=3.0 Hz, 5'-H), 4.05 (dd, 1H, J=12.0 Hz, J'=3.0 Hz), 4.62 (dddd, 1H, J=7.5 Hz, J'=6.5 Hz, J''=J'''=3.0 Hz, 4'-H), 4.70 (ddd, 1H, J=6.0 Hz, J'=4.0 Hz, J''=2.5 Hz, 2'-H), 5.88 (bs, 1H, OH), 6.01 (d, 1H, J=2.5 Hz, 1'-H), 6.15 (bs, 2H, NH$_2$), 8.30, 8.33 (2s, 2H, H-2, H-8); FAB MS, m/z 366 (M+H)$^+$, 136.

Example 14

N6-Benzoyl-5'-O-(t-butyldimethylsilyl)-2',3'-dideoxy-2'-oxoadenosine

To a stirred solution of 2.0 g (5.47 mmol) 5'-O-(t-butyldimethylsilyl)-3'-deoxyadenosine, the product of Example 13, in 11 mL of pyridine at room temperature was added 2.5 mL (21.9 mmol) of benzoyl chloride. After 2 h, 1 mL of methanol was added, the reaction mixture was diluted with ether, washed successively with water and 50% saturated aqueous sodium bicarbonated, and dried over magnesium sulfate. The organic phase was evaporated under reduced pressure and then coevaporated with several portions of n-heptane to afford 3.9 g of a foam. To a stirred solution of 3.8 g of this residue in 44 ml of dioxane were added 16.8 mL of 1N aqueous NaOH. After 2 hours 5.6 mL additional 1N aqueous NaOH were added, After a total of 2.5 hours, the reaction mixture was neutralized with acetic acid, diluted with EtOAc, washed successively with water and saturated aqueous NaCl, dried over magnesium sulfate, and then concentrated under reduced pressure. Chromatography of the residue on silica gel with a 100:0 to 95:5 EtOAc/MeOH gradient afforded 1.94 g (75%) of N6-benzoyl-5'-O-(t-butyldimethylsilyl)-3'-deoxyadenosine. To a stirred solution of 880 mg (1.87 mmol) of N6-benzoyl-5'-O-(t-butyldimethylsilyl)-3'-deoxyadenosine in 9 mL of DMSO and 9 mL of benzene at room temperature containing 1.80 g (9.37 mmol) of 1-(3-dimethylaminopropyl)-3-ethylcarbodiimide hydrochloride were added 4 portions of 0.031 mL (0.37 mmol) of dichloroacetic acid at 15 minute intervals. Fifteen minutes after the final addition, the reaction mixture was diluted with dichloromethane and washed with water adjusted to pH 3 with 1N aqueous HCl. The aqueous phase was extracted several times with dichloromethane, the combined organic extracts dried over magnesium sulfate, and then concentrated under reduced pressure. Chromatography of the residue on silica gel with a 75:25 to 100:0 EtOAc/hexane gradient afforded 694 mg (79%) of the title compound: Colorless glass. $R_f$=0.40 (SG, EtOAc); $[\alpha]_D^{23}$ −17.0° (c 1.25, CHCl$_3$); IR (CDCl$_3$) 3415, 2960, 2935, 2860, 1775, 1710, 1610, 1590, 1455, 1255, 1240, 1070 cm$^{-1}$; $^1$H-NMR (300 MHz, CDCl$_3$, TMS=0.00 ppm) δ0.05, 0.07 (2s, 6H, (CH$_3$)$_2$Si), 0.90 (s, 9H, (CH$_3$)$_3$CSi), 2.86 (dd, 1H, J=19.0 Hz, J'=7.5 Hz, 3'-H), 3.16 (dd, 1H, J=19.0 Hz, J'=7.5 Hz, 3'-H), 3.88 (dd, 1H, J=11.5 Hz, J'=4.0 Hz, 5'-H), 4.02 (dd, 1H, J=11.5 Hz, J'=3.5 Hz, 5'-H), 4.66 (dddd, 1H, J=J'=7.5 Hz, J''=4.0 Hz, J'''=3.5 Hz, 4'-H), 6.06, (s, 1H, 1'-H), 7.52 (m, 2H, m-C$_6$H$_5$), 7.61 (m, 1H, p-C$_6$H$_5$), 8.02 (m, 2H, o-C$_6$H$_5$), 8.11, 8.78 (2s, 2H, 2-H, 8-H), 9.03 (bs, 1H, NH) DCI/NH$_3$ MS, m/z 468 (M+H)$^+$, 240; exact mass calcd for C$_{23}$H$_{30}$N$_5$O$_4$Si (M+H)$^+$: 468.2067, found: 468.2067.

Example 15

N6-Benzoyl-5'-O-(t-butyldimethylsilyl)-2',3'-dideoxy-3'-(N',N'-dimethylaminomethylene)-2'-oxoadenosine To 660 mg (1.41 mmol) of N6-benzoyl-5'-O-(t-butyldimethylsilyl)-2',3'-dideoxy-2'-oxoadenosine, the product of Example 14 were added 13 mL of dimethylformamide dimethylacetal, and the resulting solution was immediately immersed in an oil bath which had been preheated to 60° C. After 15 min, the reaction mixture was cooled to room temperature and concentrated under reduced pressure. Chromatography of the residue on silica gel with a 99:1 to 93:7 chloroform/methanol gradient afforded 617 mg (84%) of the title compound: Light yellow oil. $R_f$=0.32 (SG, 95:5 CHCl$_3$:MeOH); $[\alpha]_D^{23}$ −58.1° (c 1.65, CHCl$_3$); IR (CDCl$_3$) 3405, 2955, 2930, 2855, 1705, 1610, 1585, 1450, 1250, 1210 cm$^{-1}$; $^1$H-NMR (300 MHz, CDCl$_3$, TMS=0.00 ppm) δ−0.11, −0.07 (2s, 6H, (CH$_3$)$_2$Si), 0.81 (s, 9H, (CH$_3$)$_3$CSi), 3.21 (bs, 6H, (CH$_3$)$_2$N), 3.84 (d, 2H, J=5.0 Hz, 5'-H), 5.45 (ddd, 1H, J=J'=5 Hz, J''=1 Hz, 4'-H), 6.29 (s, 1H, 1'-H), 7.52 (m, 2H, m-C$_6$H$_5$), 7.61 (m, 1H, p-C$_6$H$_5$), 7.63 (d, 1H, J=1 Hz, NCH=C), 8.02 (m, 2H, o-C$_6$H$_5$), 8.08 (s, 1H, 8-H), 8.84 (s, 1H, 2-H), 9.01 (bs, 1H, NH); FAB MS, m/z 523 (M+H)$^+$, 240.

Example 16

N6-Benzoyl-5'-O-(t-butyldimethylsilyl)-2',3'-dideoxy-3'-diazo-2'-oxoadenosine A solution of trifluoromethanesulfonyl azide in 50 mL 1,2-dichloroethane (prepared from 6.0 mL (35.4 mmol) of trifluoromethanesulfonic acid and 13.6 g of sodium azide according to the procedure of Step 5 of Example 22) was added to 600 mg (1.148 mmol) of N6-benzoyl-5'-O-(t-butyldimethylsilyl)-2',3'-dideoxy-3'-(N',N'-dimethylaminomethylene)-2'-oxoadenosine, the product of Example 15, and the resulting solution was heated a 60° C. for 2 hours. The reaction mixture was then concentrated to a volume of 10 mL and applied to a silica gel column. Elution with a 1:3 to 100:0 EtOAc/hexane gradient, followed by elution with 1:9 MeOH/EtOAc afforded 409 mg (72%) of the title compound: Light yellow amorphous solid. $R_f$=0.34 (SG, 7:3 EtOAc:hexane); $[\alpha]D^{25}$ −57.5° (c 1.31, CHCl$_3$); IR (CDCl$_3$) 3405, 3005, 2955, 2930, 2855, 2115, 1700, 1610, 1590, 1455, 1365, 1330, 1250 cm$^{-1}$; $^1$H-NMR (300 MHz, CDCl$_3$, TMS=0.00 ppm) δ0.10, 0.11 (2s, 6H, (CH$_3$)$_2$Si), 0.91 (s, 9H, (CH$_3$)$_3$CSi), 4.02 (dd, 1H, J=9.5 Hz, J'=5.0 Hz, 5'-H), H), 4.06 (dd, 1H, J=9.5 Hz, J'=7.5 Hz, 5'-H), 5.44 (dd, 1H, J=7.5 Hz, J'=5.0 Hz, 4'-H), 6.37 (s, 1H, 1'-H), 7.53 (m, 2H, m-C$_6$H$_5$), 7.62 (m, 1H, p-C$_6$H$_5$), 8.02 (m, 2H, o-C$_6$H$_5$), 8.07, 8.82 (2s, 2H, H-2, H-8), 9.00 (bs, 1-H, NH); FAB MS, m/z 494 (M+H)$^+$, 240; exact mass calcd for C$_{23}$H$_{28}$N$_7$O$_4$Si (M+H)$^+$: 494.1972, found: 494.1971.

Example 17

N6-Benzoyl-9-((2'R,3'R,4'S)-3'-Methoxycarbonyl-4'-(t-butyldimethylsilyloxymethyl)-2'-oxetanyl)adenine A solution of 104 mg (0.211 mmol) of N6-benzoyl-5'-O-(t-butyldimethylsilyl)-2',3'-dideoxy-3'-diazo-2'-oxoadenosine, the product of Example 16, in 60 mL of methanol was purged with argon for 60 minutes and then irradiated with a 450 W Hanovia mercury arc lamp through a pyrex filter for 30 minutes at room temperature. An additional 114 mg (0.231 mmol) N6-benzoyl-5'-O-(t-butyldimethylsilyl)-2',3'-dideoxy-3'-diazo-2'-oxoadenosine, the product of Example 16, in 55 mL of methanol was purged with argon for 60 minutes and then irradiated with a 450 W Hanovia mercury arc lamp through a pyrex filter for 25 minutes at room temperature. The resulting solutions were combined and concentrated under reduced pressure. Chromatography of the residue on silica gel with a 9:1 to 4:6 dichlormethane/acetone gradient followed by further chromatography on silica gel with 8:2 EtOAC/hexane afforded 53 mg (24%) of the title compound: Colorless oil. $R_f$=0.41 (SG, 7:3 EtOAc:hexane); $[\alpha]D^{25}$ −18.4° (c 1.59, CHCl$_3$); IR (CDCl$_3$) 3405, 2955, 2930, 2860, 1740, 1710, 1610, 1585, 1455, 1250, 1240, 1215 cm$^{-1}$; $^1$H-NMR (300 MHz, CDCl$_3$, TMS= 0.00 ppm) δ0.18, 0.20 (2s, 6H, (CH$_3$)$_2$Si), 0.97 (s, 9H, (CH$_3$)$_3$CSi), 3.81 (s, 3H, OCH$_3$), 3.94 (dd, 1H, J=12.5 Hz, J'=3.0 Hz, 5'-H), 4.13 (dd, 1H, J=12.5 Hz, J'=2.5 Hz, 5'-H), 4.54 (dd, 1H, J=7.0 Hz, J'=6.5 Hz, 2'-H), 4.90 (ddd, 1H, J=7.0 Hz, J'=3.0 Hz, J''=2.5 Hz, 4'-H), 6.86 (d, 1H, 6.5 Hz, 1'-H), 7.54 (m, 2H, m-C$_6$H$_5$), 7.62 (m, 1H, p-C$_6$H$_5$), 8.03 (m, 2H, o-C$_6$H$_5$), 8.68 (s, 1H, H-8), 8.84 (s, 1H, H-2), 9.03 (bs, 1H, NH); DCI/NH$_3$ MS, m/z 498 (M+H)$^+$, 240; exact mass calcd for C$_{24}$H$_{32}$N$_5$O$_5$Si (M+H)$^+$: 498.2173, found (FAB MS): 498.2174.

Example 18

9-((2'R,3'R,4'S)-3'-Hydroxymethyl-4', -butyldimethylsilyloxymethyl)-2'-oxetanyl)adenine To a stirred solution of 32 mg (0.064 mmol) of N6-benzoyl-9-((2'R, 3'R, 4'S)-3'-methoxycarbonyl-4'-(t-butyldimethylsilyloxymethyl)-2'-oxetanyl)adenine, the product of Example 17, in 2 mL of EtOH were added 32 mg (0.845 mmol) of sodium borohydride. After 5 hours at room temperature, the reaction mixture was packed in a −20° C. freezer for 70 hours, and then allowed to warm to room temperature. The reaction mixture was diluted with 50 mL of saturated aqueous NaCl, extracted with 3×75 mL portions of dichloromethane, dried over magnesium sulfate, and then concentrated under reduced pressure. Chromatography of the residue on silica gel with 95:5 chloroform/methanol afforded 17.2 mg (74%) of the title compound: Colorless oil. $R_f$=0.31 (SG, 90:10 CHCl$_3$:MeOH); $[\alpha]D^{25}$ +2.7° (c 0.59, CHCl$_3$); IR (CDCl$_3$) 3525, 3415, 2955, 2925, 2855, 1630, 1580, 1470, 1250 cm$^{-1}$; $^1$H-NMR (300 MHz, CDCl$_3$, TMS=0.00 ppm) δ 0.11, 0.13 (2s, 6H, (CH$_3$)$_2$Si), 0.89 (s, 9H, (CH$_3$)$_3$CSi), 2.07 (bs, 1H, OH), 3.58 (dddd, 1H, J=8.0 Hz, J'=6.5 Hz, J''=5.5 Hz, J'''=4.5 Hz, 2'-H ), 3.77 (dd, 1H, J=12.5 Hz, J'=3.0 Hz, 5'-H), 3.91 (dd, 1H, J=11.5 Hz, J'=4.5 Hz, 3'-H), 4.00 (dd, 1H, J=12.5 Hz, J'=3.0 Hz, 5'-H), 4.04 (dd, 1H, J=11.5 Hz, J'=8.0, 3'-H), 4.69 (ddd, 1H, J=6.5 Hz, J'=J''=3.0 Hz, 4'-H), 5.84 (bs, 2H, NH$_2$), 6.48 (d, 1H, J=5.5 Hz, 1'-H), 8.31, 8.42 (2s, 2H, H-2, H-8); DCI/NH$_3$ MS, m/z 366 (M+H)$^+$.

Example 19

9-((2'R,3'R,4'S)-3',4'-Bis(hydroxymethyl)-2'-oxetanyl)adenine

To a solution of 11.8 mg (0.0323 mmol) of 9-((2'R,3'R,4'S)-3'-hydroxymethyl-4'-(t-butyldimethylsilyloxymethyl)-2'-oxetanyl)adenine, the product of Example 18, in 2 mL of methanol at room temperature were added 0.008 mL of chlorotrimethylsilane. After 105 minutes, the reaction mixture was diluted 4 mL of methanol and then treated with a sufficient amount of a highly cross lined basic ion exchange resin (hydroxide form) so that the apparent pH of the solution on wet pH paper was 8. The resin was removed by filtration, and the filtrate concentrated under reduced pressure to afford 7.7 mg (95%) of the title compound: Amorphous white solid. $R_f$=0.20 (SG, 80:20 CHCl$_3$:MeOH); $[\alpha]D^{25}$ −41.3° (c 0.65, pyridine); $^1$H-NMR (300 MHz, D$_2$O, HOD=4.80 ppm) δ3.81 (dddd, 1H, J=6 Hz, J'=6 Hz, J''=6 Hz, J'''=6 Hz, 2'-H), 3.84 (dd, 1H, J=14 Hz, J'=3.0 Hz, 5'-H), 3.90 (dd, 1H, J=14 Hz, J'=6 Hz, 3'-H), 3.93 (dd, 1H, J=14.0 Hz, J'=2.5 Hz, 5'-H), 3.94 (dd, 1H, J=14 Hz, J'=6 Hz, 3'-H), 4.78 (ddd, 1H, J=6.0 Hz, J'=3.0 Hz, J''=2.5 Hz, 4'-H), 6.47 (d, 1H, J=6.0 Hz, 1'-H), 8.12, 8.53 (2S, 2H, H-2, H-8); $^{13}$C-NMR (125.8 MHZ, D$_2$O, CH$_3$CN=1.40 ppm,) δ45.17, 59.61, 63.06, 79.83, 82.32, 119.10, 141.22, 148.94, 153.22, 156.08; FAB MS, m/z 252 (M+H)$^+$.

Example 20

9-((2'R,3'R,4'S)-3',4'-Bis(hydroxymethyl)-2'-oxetanyl)-guanine

This compound was prepared by substituting 5'-O-(t-butyldimethylsilyl)-3'-deoxyguanosine (obtained by the treatment of 3'-deoxyguanosine with 1.2 equivalents of t-butyldimethylsilyl chloride in pyridine) for 5'-O-(t-butyldimethylsilyl)-3'-deoxyadenosine in Example 13 and following the procedures disclosed in Examples 13–19.

Example 21

1-([2'R, 3'R, 4'S]-3',4'-Bis(hydroxymethyl)-2'-oxetanyl)5-methyluracil

Step 1: 5-Methyl-3'-deoxyuridine

2',5'-bis(O-(4''-Chloro)benzoyl)-5-methyl-3'-deoxyuridine (M. Saneyoshi, et al. *Chem Pharm Bull*, 30, 2223–7 (1982)) was deprotected in methanolic sodium methoxide. The 2',5'-bis(O-(4''-chloro)benzoyl)-5-methyl-3'-deoxyuridine (12.53 g, 24.19 mmol) was dissolved in 1 L of methanol (MeOH) containing 2.613 g (48.38 mmol) of sodium methoxide. The reaction mixture was stirred at ambient temperature for approximately 1.5 h. At this time TLC analysis on silica gel plates eluted with 10% MeOH in methylene chloride indicated that the reaction had gone to completion. The solution was concentrated under reduced pressure and diluted with water. The aqueous solution was neutralized with Amberlite IR-120® acidic resin and the resultant suspension filtered. The filtrate was concentrated under reduced pressure and the residue taken up in dry pyridine. The pyridine was removed in vacuo and the residue redissolved in dry pyridine and reconcentrated in vacuo. The residue was dried in vacuo for approximately 64 h at ambient temperature to yield 8.6 g of the title compound, which was taken on to the next step without purification.

Step 2: 5'-O-(t-Butyldimethylsilyl)-5-methyl-3'-deoxyuridine

5-Methyl-3'-deoxyuridine, from Step 1, was dissolved in 150 mL of dry pyridine and 3.6 g (24 mmol) of t-butyldimethylsilyl chloride was added in 4 portions at 4 times (t): t=0 h, t=2 h, t=3 h and at t=3.75 h. After 4.5 h, 8 mL of methanol was added to the reaction mixture and the reaction mixture was stirred for 0.5 h, then concentrated under reduced pressure to approximately 25% of volume. The concentrated reaction mixture was diluted with ethyl acetate, washed with dilute aqueous sodium bicarbonate solution and then concentrated under reduced pressure. The residue was purified by column chromatography on a 5 cm×37 cm silica gel column eluted with 90% ethyl acetate in hexane. The fractions containing the desired product were combined and concentrated in vacuo to give 7.27 g (84.4% yield based on 24.19 mmol of 2',5'-bis(O-(4''-chloro)benzoyl)-5-methyl-3'-deoxyuridine) of 5'-O-(t-butyldimethylsilyl)-5-methyl-3'-deoxyuridine, $[\alpha]_D^{23} = -19.6°$ (c, 1.42, MeOH). Analysis calculated for $C_{16}H_{28}N_2O_5Si$: C, 53.98; H, 7.91; N, 7.87. Found: C, 54.01; H, 7.85; N, 7.79.

Step 3: 5'-O-(t-Butyldimethylsilyl)-2',3'-dideoxy-5-methyl-2'-oxo-uridine

Chromium trioxide (7.63 g, 76.3 mmol) was added to 150 mL of dry methylene chloride containing 12.059 g (152.6 mmol) of pyridine. The mixture was stirred for 15 minutes. In a separate flask, 793 mg (19.08 mmol) of 5'-O-(t-butyldimethylsilyl)-5-methyl-3'-deoxyuridine from Step 2 was dissolved in approximately 100 mL of methylene chloride. The chromium trioxide-pyridine solution was added to the solution of 5'-(t-butyldimethylsilyl)-5-methyl-3'-deoxy-uridine and 1.946 g (19.08 mmol) of acetic anhydride was added immediately. After stirring at ambient temperature for 0.5 h, the reaction mixture was diluted with approximately 250 mL of ethyl acetate then filtered through Celite filter aid and through florisil eluted with ethyl acetate. The solvent was evaporated and the residue purified on silica gel eluted with 90% ethyl acetate in hexanes. The title compound was obtained in 59.6% yield (4.08 g) $[\alpha]_D^{23} = +38.0°$ (c, 1.31, MeOH). Analysis calculated for $C_{16}H_{26}N_2O_5Si$: C, 54.24; H, 7.34; N, 7.91. Found: C, 54.25; H, 7.36; N, 7.88

Step 4: 5'-O-(t-Butyldimethylsilyl)-2',3'-dideoxy-3'-(N,N-dimethylaminomethylene)-5-methyl-2'-oxo-uridine 5'-O-(t-Butyldimethylsilyl)-2',3'-dideoxy-5-methyl-2'-oxo-uridine (3.854 g, 10.9 mmol) from Step 3 was dissolved in 50 mL of dry dimethylformamide (DMF) and 1.74 mL (1.56 g, 13.1 mmol) of N,N-dimethylformamide dimethylacetal was added. The reaction mixture was heated in an oil bath at 50° C. for 40 min. The solvent was evaporated in vacuo and the residue purified on a silica gel column, the product eluting with 5% methanol in methylene chloride to give 2.512 g (56.3% yield) of the title compound, $[\alpha]_D^{23} = -84.2°$ (C, 1.44, MeOH). DCI MS M/Z: (M+H)+ 410.

Step 5: 5'-O-(t-Butyldimethylsilyl)-2',3'-dideoxy-3'-diazo-5-methyl-2'-oxo-uridine 5'-O-(t-Butyldimethylsilyl)-2',3'-dideoxy-3'-(N,N-dimethylamino-methylene)-5-methyl-2'-oxo-uridine (2.512 g, 6.1 mmol), from Step 4, was dissolved in 10 mL of 1,2-dichloroethane and a freshly prepared solution of trifluoromethanesulfonyl azide was added. The trifluoromethanesulfonyl azide solution was prepared as follows: Sodium azide (19.8 g, 0.305 mol) was dissolved in 50 mL of water and 62 mL of 1,2-dichloroethane was added. The mixture was cooled in an ice bath and 17.2 g (61 mmol) of trifluormethanesulfonyl anhydride was added dropwise. After the addition was complete, the mixture was stirred at 0° C. for 2 h. 1,2-Dichloroethane (10 mL) was added, the layers separated and the aqueous layer extracted with 2×5 mL of 1,2-dichloroethane. The combined organic layer was washed with 1N sodium hydroxide solution and brine, dried over anhydrous magnesium sulfate and filtered.

The reaction mixture was heated in an oil bath at 60° C. for 2 h and concentrated (to approximately 30 mL) under reduced pressure. The solution was chromatographed on a silica gel column (3.0×30 cm) eluted with 50% ethyl acetate in hexanes. The product obtained was repurified on a silica gel column (3.0×31 cm) eluted with 2% methanol in methylene chloride to give 1.74 g (75.1% yield) of the title compound, $[\alpha]_D^{23} = +3.7°$ (c, 1.23, MeOH). Analysis calculated for $C_{16}H_{24}N_4O_5Si$: C, 50.28; H, 6.30; N, 14.73. Found: C, 50.28; H, 6.30; N, 14.73.

Step 6: 1-([2'R,3'R, 4'S]-4'-((t-Butyldimethylsilyl)oxymethyl)-3'-methoxycarbonyl-2'-oxetanyl)-5-methyluracil 5'-O-(t-Butyldimethylsilyl)-2',3'-dideoxy-3'-diazo-5-methyl-2'-oxo-uridine (1.638 g, 4.31 mmol), from Step 5, was dissolved in 1.5 L of methanol. The methanol solution was added to a water-cooled pyrex photolysis cell and nitrogen was passed through for 20 minutes. It was then irradiated in 150 mL batches for 20 minutes with a 450 W Hanovia lamp. The solutions were agitated during the irradiation by bubbling nitrogen through them. The individual batches were checked by TLC (on silica gel plates eluted with 90% ethyl acetate in hexanes) then combined and concentrated under reduced pressure. The residue was purified by chromatography on silica gel eluted with 50% ethyl acetate in hexanes to give 0.858 g (51.8% yield) of the title compound, $[\alpha]_D^{23} = -2.9°$ (c, 1.19, MeOH). Analysis calculated for $C_{17}H_{28}N_2O_6Si$: C, 53.12; H, 7.29; N, 7.29. Found: C, 52.97; H, 7.28; N, 7.26.

Step 7: 1-([2'R,3'R,4'S]-4'-((t-Butyldimethylsilyl)oxymethyl)-3'-hydroxymethyl-2'-oxetanyl)5-methyluracil 1-([2'R, 3'R,4'S]-4'-((t-Butyldimethylsilyl)oxymethyl)-3'-methoxycarbonyl-2'-oxetanyl)-5-methyl-uracil (0.597 g, 1.55 mmol), from Step 6, was dissolved in 10 mL of ethanol with cooling in an ice bath. Sodium borohydride (0.586 g, 15.5 mmol) was added and the reaction mixture was stirred for 0.5 h. The reaction mixture was then diluted with methylene chloride and washed with pH 6 phosphate buffer solution. The organic layer was washed with brine, dried over anhydrous magnesium sulfate, filtered and concentrated under reduced pressure. The residue was purified on a silica gel column (3×18 cm) eluted with 90% ethyl acetate in hexanes to give 0.28 g (50.7% yield) of the title compound, $[\alpha]_D^{23} = +14.9°$ (c, 0.57, MeOH). Analysis calculated for $C_{16}H_{28}N_2O_5Si$: C, 53.98; H, 7.92; N, 7.87. Found: C, 53.77; H, 7.86; N, 7.77.

Step 8: 1-([2'R,3'R,4'S]-3',4'-Bis(hydroxymethyl)-2'-oxetanyl)-5-methyl-uracil 1-([2'R,3'R,4'S]-4'-((t-Butyldimethylsilyl)oxymethyl)-3'-hydroxymethyl-2'-oxetanyl)-5-methyl-uracil (0.102 g, 0.287 mol) was dissolved in dry THF and 90.45 mg (0.29 mmol) of tetra-n-butylammonium fluoride was added. The mixture was stirred at ambient temperature for 2 h and 16.4 µL of glacial acetic acid was added. The resultant solution was concentrated in vacuo. Water was added to remove the residual THF as an azeotrope with water. The residue was dissolved in water. A reverse phase chromatography column was prepared by slurrying 43 g of C-18 packing material in methanol and pouring the slurry into a 2.2×26 cm column. The column was washed with 400 mL of water prior to applying the aqueous solution of the crude product. The column was eluted with 180 mL of water, 100 mL of 5% methanol in water and 50 mL of 10% methanol in water to give 66 mg (95% yield) of the title compound, $[\alpha]_D^{23} = +28.06°$ (c 0.955, MeOH); FAB MS, M/Z: 243 (M+H)+; exact mass calculated for $C_{10}H_{15}N_2O_5$: 243 0981 (M+H)+, Found: 243.0982; $^1$H NMR (CD$_3$OD) ∂1.91 (d, 3H, J=1.5 Hz), 3.30 (m, 1H, obscured by CD$_2$HOD), 3.64 (dd, 1H, J=13 Hz, J''=3 Hz), 3.74 (dd, 1H, J=11.5 Hz, J'=5 Hz), 3.79 (dd, 1H, J=11.5 Hz, J'=5 Hz), 3.84 (dd, 1H, J=13 Hz, J'=2.5 Hz), 4.55 (ddd, 1H, J=7 Hz, J'=2.5 Hz, J''=3 Hz), 6.34 (d, 1H, J=6 Hz), 8.33 (q, 1H, J=1.5 Hz).

Example 22

1-([2'R,3'R,4'S]-3',4'-Bis(hydroxymethyl)-2'-oxetanyl)-cytosine

Step 1: 4-(N-Acetyl)-2',5'-bis(O-(4''-chloro)benzoyl)-3'-deoxycytidine

4-N-Acetyl cytosine (1.935 g, 12.6 mmol), prepared as described by P. Angibeaud, et al. in *Carbohydrate Research*, 78, 195–204 (1980), was dissolved in 100 mL of hexamethyldisilazane containing 50 mg of ammonium sulfate and the solution was heated at reflux temperature for 3 h. Solvent was then removed by azeotropic distillation with toluene. The residue was dried in vacuo for 1 h and then dissolved in 30 mL of acetonitrile. 1-O-Acetyl-2,5-bis(O-(4'-chloro)benzoyl)-3'-deoxyribose (5.145 g, 11.4 mmol) dissolved in 30 mL of acetonitrile was added, followed by 3.85 g (1.73 mL, 14.8 mmol) of tin tetrachloride. The solution was stirred at ambient temperature overnight and the solvents evaporated under reduced pressure. Saturated aqueous sodium bicarbonate solution was added to neutralize the residue and ethanol was added before removing the water under vacuum. The solid residue was extracted three times with hot acetone. The combined filtrate (the acetone solution) was concentrated under reduced pressure and the residue triturated with isopropyl alcohol to give 3.70 g of the desired product. A small amount (0.438 g) of the desired product also crystallized from the isopropyl alcohol "mother liquor". The solid which had been extracted with hot acetone was found to contain additional product which was extracted with two portions of methylene chloride. The total yield of 4-(N-acetyl)-2',5'-bis(O-(4''-chloro)benzoyl)-3'-deoxycytidine was 5.01 g (84.5% yield).

The 1-O-acetyl-2,5-bis(O-(4'-chloro)benzoyl)-3'-deoxyribose used in the above synthesis was prepared as follows: Adenosine was converted to 2',3'-dideoxy-2',3'-epoxyadenosine by the method described by F. Hansske and J. Robins in *Tetrahedron Letters*, 4295–8 (1985) using 100:1 acetonitrile:water as solvent, not 10:1 as reported. The epoxide was reduced to 3'-deoxyadenine as described in the same reference, using 2.1 equivalents of lithium triethylborohydride in THF, instead of the 12.5 equivalents of lithium triethylborohydride in DMSO reported. Benzoyl protecting groups were introduced as described by M. Sanyoshi, et al. in *Chem Pharm Bull*, 30, 2223–7 (1982) and the sugar was cleaved from the purine base as described in the same reference, with the exception that 1 equivalent, not 15 equivalents as reported) of concentrated sulfuric acid was used.

Step 2: 5'-O-(t-Butyldimethylsilyl)-3'-deoxycytidine 4-(N-Acetyl)-2',5'-bis(O-(4''-chloro)benzoyl)-3'-deoxycytidine (5.0 g, 9.6 mmol), from Step 1, was treated with 200 mL of methanol and 200 mL of concentrated ammonium hydroxide at 55° C. for 5.5 h. The solvent was evaporated under reduced pressure and the residue dried under vacuum overnight. The dry residue was dissolved in 40 mL of dry pyridine and 1.447 g (9.6 mmol) of t-butyldimethylsilyl chloride was added. After the reaction mixture was stirred at ambient temperature for 50 minutes a second 9.6 mmol portion of t-butyldimethylsilyl chloride was added, followed by 1.632 g (24 mmol) of imidazole. After stirring the reaction mixture for approximately 3 h, 5 mL of methanol was added and the solution stirred for approximately 0.5 h. The solution was concentrated under reduced pressure to approximately ⅓ of original volume and diluted with methylene chloride. The resultant solution was partitioned between saturated aqueous sodium bicarbonate and ethyl acetate and the layers separated. The organic layer was dried over anhydrous magnesium sulfate, filtered and concentrated in vacuo. The residue was purified on a silica gel column (3×30 cm) eluted with 10% methanol in methylene chloride. Fractions containing the incompletely purified product were combined, concentrated under reduced pressure and rechromatographed on a silica gel column (2×40 cm) eluted with 10% methanol in methylene chloride to give the desired product. The pure product from the first and second column were combined to give 1.38 g (42% yield) of 5'-O-(t-butyldimethylsilyl)-3'-deoxycytidine. MS DCI M/Z: 342 (M+H)+.

Step 3: 5'-O-(t-Butyldimethylsilyl)-2',3'-dideoxy-4-(N-(N',N'-dimethyl)aminomethylene)-2'-oxo-cytidine 5'-O-(t-Butyldimethylsilyl)-3'-deoxycytidine (0.49 g, 1.473 mmol), from Step 2, was dissolved in 15 mL of dimethyformamide containing 1.33 mL (10 mmol) of N,N-dimethylformamide dimethyl acetal and the solution was stirred at ambient temperature for 4 h. The solvent was removed in vacuo to give 5'-O-(t-butyldimethylsilyl)-3'-deoxy-4-(N-(N',N'-dimethyl)aminomethylene)-cytidine which was taken on without purification. Dimethylsulfoxide (209 µL, 2.70 mmol) was added to 8 mL of dry methylene chloride and the solution was cooled in a dry ice-acetone bath. Oxalyl chloride (193 µL, 2.21 mmol) was added, followed by (after 17 minutes) 5'-O-(t-butyldimethylsilyl)-3'-deoxy- 4-(N-(N',N'-dimethyl)aminomethylene)-cytidine dissolved in 4 mL of methylene chloride. After stirring the reaction mixture for 35 minutes at −78° C. 819 μL of triethylamine was added and after an additional 45 minutes, approximately 3 mL of 10% aqueous citric acid solution was added. The reaction mixture was then allowed to warm to ambient temperature and diluted with methylene chloride, washed with 10% citric acid solution, saturated aqueous sodium bicarbonate solution and brine, dried over anhydrous magnesium sulfate, filtered and concentrated under reduced pressure to give 0.61 g of the title compound, which was taken on to the next step without purification.

Step 4: 5'-O-(t-Butyldimethylsilyl)-2',3'-dideoxy-4-(N-N',N'-dimethylamino)methylene)-3'-(N',N'-dimethylaminomethylene)-2'-oxo-cytidine 5'-O-(t-Butyldimethylsilyl)-2',3'-dideoxy-4-(N-(N',N'-dimethyl)aminomethylene)-2'-oxo-cytidine from Step 3 was dissolved in 5 mL of dimethylformamide and 1.37 mL (10.3 mmol) of N,N-dimethylformamide dimethyl acetal was added. The solution was stirred at ambient temperature for 4.33 h and concentrated in vacuo to give 0.66 g of title compound, which was taken on to the next step without purification.

Step 5: 5'-O-(t-Butyldimethylsilyl)-3'-diazo-2',3'-dideoxy-4-(N-(N',N'-dimethylamino)methylene)-2'-oxo-cytidine Trifluoromethanesulfonyl azide was prepared as follows: Trifluoromethanesulfonyl anhydride (3.72 mL, 22.1 mmol) was added slowly to a mixture of 7.182 g (10.5 mmol) of sodium azide in 18 mL of water and 21 mL of 1,2-dichloroethane, cooled in an ice bath. The mixture was stirred in an ice bath for 2 h, diluted with 4 mL of 1,2-dichloroethane and the layers separated. The aqueous layer was extracted with 2×4 mL of 1,2-dichloroethane. The combined organic extract was washed with 1M aqueous sodium hydroxide solution and brine, dried over anhydrous magnesium sulfate. 5'-O-(t-Butyldimethylsilyl)-2',3'-dideoxy-4-(N-(N', N'-dimethylamino)methylene)-3'-(N',N'-dimethylamino)methylene)-2'-oxo-cytidine from Step 4 was added to 20 mL of the trifluoromethanesulfonyl azide solution and the reaction mixture was heated in a 60° C. oil bath for 2 h, filtered and partially concentrated under reduced pressure. The residue was purified by flash chromatography on a silica gel column (1.5×33 cm) eluted with 5% methanol in methylene chloride to give the title compound MS DCI M/Z: 421 (M+H)+.

Step 6: 5'-O-(t-Butyldimethylsilyl)-3'-diazo-2',3'-dideoxy-2'-oxo-cytidine

5'-O-(t-Butyldimethylsilyl)-3'-diazo-2',3'-dideoxy-4-(N-(N',N'-dimethylamino)methylene)-2'-oxo-cytidine (1.4 g (3.3 mmol), from Step 5, was dissolved in 500 mL of methanol and 104 mg pyridinium p-tosylate was added. The resultant solution was allowed to stand at ambient temperature overnight then concentrated to approximately 75 mL, diluted with ethyl acetate, washed with saturated aqueous sodium bicarbonate solution and brine, dried over anhydrous magnesium sulfate, filtered and concentrated. The residue was purified on a silica gel column (3×24 cm) eluted with 5% methanol in methylene chloride, followed by 10% methanol in methylene chloride to give 709 mg (59% yield) of the title compound. MS DCI M/Z: 366 (M+H)+.

Step 7: 1-([2'R,3'R,4'S]-4'-((t-Butyldimethylsilyl)oxymethyl)-3'-methoxycarbonyl-2'-oxetanyl)cytosine 5'-O-(t-Butyldimethylsilyl)-3'-diazo-2',3'-dideoxy-2'-oxo-cytidine (0.610 g, 1.67 mmol), from Step 5, was dissolved in 650 mL of methanol. The methanol solution was added to a water-cooled pyrex photolysis cell and nitrogen was passed through for 20 minutes. It was then irradiated in 160 mL batches for 20 minutes with a 450 W Hanovia lamp. The solutions were agitated during the irradiation by bubbling nitrogen through them. The individual batches were checked by TLC (on silica gel plates eluted with 90% ethyl acetate in hexanes) then combined and concentrated under reduced pressure. The residue was purified by chromatography on silica gel (1.5×30 cm) eluted with 5% methanol in methylene chloride to give 188 mg (30% yield) of the title compound. MS DCI M/Z: 370 (M+H)+.

Step 8: 1-([2'R,3'R,4'S]-4'-((t-Butyldimethylsilyl)oxymethyl)-3'-hydroxymethyl-2'-oxetanyl)cytosine 1-([2'R, 3'R, 4'S]-4'-((t-Butyldimethylsilyl)oxymethyl)-3'-methoxycarbonyl-2'-oxetanyl)cytosine (249 mg, 0.674 mmol) (obtained by combining the product of Step 6 above and another batch of the same product prepared by the same method) was dissolved in 25 mL of absolute ethanol and the resultant solution was cooled in an ice bath. Sodium borohydride (260 mg, 6.87 mmol) was added to the above solution and the reaction mixture was stirred for 2.25 h. The reaction mixture was then diluted with 125 mL of methylene chloride and the resultant solution was washed with pH 6 phosphate buffer. The phases were separated and the organic layer was washed with brine, dried over anhydrous magnesium sulfate, filtered and concentrated under reduced pressure. The residue (236 mg) was purified by flash chromatography on a silica gel column (1.0×22 cm) eluted with a step-gradient of 5%, 10% and 20% methanol in chloroform to afford 180 mg (78.3% yield) of the title compound MS DCI M/Z: 342 (M+H)+, 370 (M+C$_2$H$_5$)+

Step 9: 1-([2'R,3'R,4'S]-3',4'-Bis(hydroxymethyl)-2'-oxetanyl)cytosine 1-([2'R, 3'R, 4'S]-4'-((t-Butyldimethylsilyl)oxymethyl)-3'-hydroxymethyl-2'-oxetanyl)cytosine (83 mg, 0.243 mmol) from Step 7 above, was dissolved in 2 mL of dry THF and 77 mg (0.243 mmol) of n-butylammonium fluoride was added. Immediately upon addition of the n-butylammonium fluoride, the solution became turbid and a precipitate formed. After stirring at ambient temperature for 0.5 h, the reaction mixture was diluted with methylene chloride containing 14 μL (0.243 mmol) of glacial acetic acid. Methanol was added to form a solution. The solvents were evaporated in vacuo and the residue dissolved in water. The aqueous solution was purified on a reverse phase (C$_{18}$) column packed with water and eluted with water followed by 5% methanol in water to afford 36.9 mg (66.9% yield) of the title compound, [α]$_D^{23}$= +64.4° (c, 0.83, H$_2$O). MS DCI M/Z: 228 (M+H)+. $^1$H NMR (CD$_3$OD) δ3.07 (dddd, 1H, J=J'=J''=J'''=6 Hz), 3.61 (dd, 1H, J=13 Hz, J'=3 Hz), 3.80 (dd, 1H, J=13 Hz, J'=3 Hz), 3.83 (d, 2H, J=6 Hz), 4.60 (ddd, 1H, J=6 Hz, J'=J''=3 Hz), 5.94 (d, 1H, J=8 Hz), 6.20 (d, 1H, J=6 Hz), 8.30 (d, 1H, J=8 Hz).

Example 23

1-([2'R,3'R,4'S]-3',4'-Bis(hydroxymethyl)-2'-oxetanyl)uracil

Step 1: 5'-O-Benzoyl-3-deoxy-2'-epi-3'-iodouridine 1-(5'-O-Benzoyl-2',3'-epoxy-β-D-lyxofuranosyl)uracil, prepared as described in Codington, et al. *J Org*

*Chem*, 27, 163 (1962), (2.0 g, 6.1 mmol), anhydrous sodium iodide (2.4 g, 16 mmol), glacial acetic acid (8.0 mL) and 2-butanone (100 mL) were combined at ambient temperature and heated at reflux temperature under nitrogen for approximately 19 h. The reaction mixture was concentrated in vacuo and the residue was triturated with 100 mL of water containing approximately 50 mg of sodium thiosulfate. The solution was decanted and then the residue was dissolved in ethyl alcohol. The ethyl alcohol solution was concentrated under reduced pressure and the residue (2.67 g) was dissolved in methanol. The methanol solution was adsorbed onto 4 g of silica gel in vacuo at 40° C. and applied to a silica gel column (2.8×50 cm). The column was eluted at 10 psi with 500 mL of 5% methanol in methylene chloride followed by 500 mL of 10% methanol in methylene chloride to give 2.4 g (86% yield) of the title compound. MS DCI: 459 $(M+H)^+$, 476 $(M+NH_4)^+$.

Step 2: 5'-O-Benzoyl-2'-epi-3'-deoxyuridine

5'-O-Benzoyl-3'-deoxy-2'-epi-3'-iodouridine (15.0 g, 32.7 mmol), from Step 1, was dissolved in 200 mL of freshly distilled tetrahydrofuran (THF) and 12.4 g (42.6 mmol) of tri-n-butyltin hydride was added. The reaction mixture was stirred at ambient temperature for 2 h under a nitrogen atmosphere. The solvent was removed in vacuo and the residue was dissolved in 1.5 L of acetonitrile. The acetonitrile solution was washed with 4×250 mL of hexane and concentrated to a white solid. The solid was dissolved in 100 mL of boiling absolute ethanol and precipitated from the ethanol solution at 4° C. The precipitate was filtered and dried to constant weight to give 9.25 g (87% yield) of the title compound. MS DCI: 333 $(M+H)^+$, 350 $(M+NH_4)^+$.

Step 3: 2'-epi-3'-Deoxyuridine

5'-O-Benzoyl-2'-epi-3'-deoxyuridine (15.0 g, 32.7 mmol) was combined with 5.65 g of anhydrous potassium carbonate in 200 mL of methanol. The mixture was stirred at ambient temperature for 2 h under a nitrogen atmosphere, neutralized with acidic resin, filtered and concentrated under reduced pressure. The residue was dissolved in dry pyridine and reconcentrated. The product was then taken on to the next step without purification.

Step 4: 5'-O-(t-Butyldimethylsilyl)-2'-epi-3'-deoxyuridine

2'-epi-3'-Deoxyuridine, from Step 3, was combined with 250 mL of dry pyridine and 10.5 g (69.7 mmol) of t-butyldimethylsilyl chloride and the resultant solution was stirred at ambient temperature overnight under a nitrogen atmosphere. Solvent was removed in vacuo and the residue (29 g) was purified by flash chromatography (2 psi) on a silica gel column (6×35 cm) eluted with 1.5 L of methylene chloride followed by 4 L of 5% methanol in methylene chloride to give 15.96 g (89% yield) of the title compound as a syrup. MS DCI: 343 $(M+H)^+$, 360 $(M+NH_4)^+$.

Step 5: 5'-O-(t-Butyldimethylsilyl)-2',3'-dideoxy-2'-oxo-uridine

Chromium trioxide (3.6 g, 36 mmol) was added to 84 mL of freshly distilled methylene chloride containing 5.8 mL of dry pyridine and the mixture was stirred for 15 minutes at ambient temperature under a nitrogen atmosphere. In a separate flask, 3.0 g (8.8 mmol) of 5'-O-(t-butyldimethylsilyl)-2'-epi-3'-deoxyuridine from Step 4 was dissolved in 60 mL of methylene chloride. The chromium trioxide-pyridine solution (63 mL) was added to the nucleoside solution, followed immediately by the addition of 2.5 mL of acetic anhydride. The reaction mixture was stirred at ambient temperature for 45 minutes under a nitrogen atmosphere, then diluted with 1 L of ethyl acetate, filtered and passed through florisil (approximately 120 mL). Solvent was removed in vacuo and the residue (3.2 g) was dissolved in 10 mL of methylene chloride and purified by flash chromatography (5 psi) on a silica gel column (2.6×43 cm) eluted with 0.5 L of methylene chloride, 0.5 L of 2% methanol in methylene chloride and 0.5 L of 5% methanol in methylene chloride to give 2.22 g (74% yield) of the title compound as a syrup. MS DCI: 341 $(M+H)^+$.

Step 6: 5'-O-(t-Butyldimethylsilyl)-2',3-(N,N-dimethylaminomethylene)-2'-oxo-uridine 5'-O-(t-Butyldimethylsilyl)-2',3'-dideoxy-2'-oxo-uridine (2.2 g, 6.45 mmol) was dissolved in 25 mL of dry dimethylformamide (DMF) and 0.85 g (7.1 mmol) of N,N-dimethylformamide dimethyl acetal was added. The reaction mixture was heated to 50° C. under a nitrogen atmosphere and stirred for 0.5 h. The solvent was removed in vacuo and the residue (3.2 g) was dissolved in methylene chloride and purified by flash chromatography (5 psi) on a silica gel column (2×25 cm) eluted with 200 mL of methylene chloride, 200 mL of 2% methanol in methylene chloride and 200 mL of 5% methanol in methylene chloride to give 1.78 g (70% yield) of the title compound. MS DCI: 396 $(M+H)^+$, 418 $(M+Na)^+$ Step 7: 5'-O-(t-Butyldimethylsilyl)-2',3'-dideoxy-3'-diazo-2'-oxo-uridine Trifluoromethanesulfonyl anhydride (12.7 g, 7.6 mL, 45 mmol) was added slowly to a solution of 14.4 g of sodium azide in water: 1,2-dichloroethane (1:1, 45 mL/45mL) at 0° C. This mixture was stirred vigorously for 3 h under a nitrogen atmosphere, then diluted with 45 mL of water. The layers were separated and the aqueous layer was extracted with 2×45 mL of 1,2-dichloroethane. The combined organic layer was washed with 45 mL of 5% aqueous sodium bicarbonate solution, 45 mL of brine, dried over anhydrous magnesium sulfate and filtered to yield 135 mL of trifluoromethanesulfonyl azide solution.

5'-O-(t-Butyldimethylsilyl)-2',3'-dideoxy-3'-(N,N-dimethylamino-methylene)-2'-oxo-uridine (1.78 g, 4.5 mmol), from Step 6, was added to the trifluoromethanesulfonyl azide solution and the reaction mixture was heated at 60° C. for 2.5 h under a nitrogen atmosphere. The solvents were evaporated in vacuo to a syrup (2.8 g) which was dissolved in 10 mL of methylene chloride and purified by flash chromatography (5 psi) on a silica gel column (2×35 cm) eluted with 200 mL of methylene chloride, 200 mL of 1% methanol in methylene chloride, 200 mL of 2% methanol in methylene chloride and 3% methanol in methylene chloride to give 1.27 g (77% yield) of the title compound. MS DCI: 367 $(M+H)^+$.

Step 8: 1-[2'R,3'R,4'S]-4'-((t-Butyldimethylsilyl)oxymethyl)-3'-methoxycarbonyl-2'-oxetanyl)uracil 5'-O-(t-Butyldimethylsilyl)-2',3'-dideoxy-3'-diazo-2'-oxo-uridine (1.27 g, 3.47 mmol), from Step 7, was dissolved in 155 mL of methanol and nitrogen gas was passed through the methanol solution for approximately 20 minutes. The methanol solution was then irradiated by a 450 W Hanovia lamp for 25 minutes in a water-cooled pyrex photolysis cell then concentrated under reduced pressure. The residue (1.26 g) was dissolved in 5mL of methylene chloride and purified by flash chromatography (5 psi) on a silica gel column eluted with 250 mL of methylene chloride, 500 mL of 1% methanol in methylene chloride and 500 mL of 2% methanol in methylene chloride to give two isomeric products. The title compound, the (2'R,3'R,4'S) isomer, was obtained in 47% yield (604 mg). MS DCI: 371 (M+H)+. (2'R,3'R,4'S) isomer, was obtained in 47% yield (604 mg).

Alternate procedure: Base-catalyzed equilibration of the 3'-carbomethoxy epimers (produced by the photochemically induced ring contraction of the diazoketone of step 7) to yield a greater predominance of the (2'R,3'R,4'S) isomer To a stirred solution of 3.89 g of the crude photolysate (produced by irradiating 3.6 g (9.8 mmol) of the diazoketone of Step 7 of Example 23 in 3.3 L of MeOH according to the procedure of Step 6 of Example 21 followed by evaporation of methanol) in 75 mL of acetonitrile was added 1.76 mL (11.8 mmol) of 1,8-diazabicyclo[5.4.0]undec-7-ene, and the resulting mixture was heated at 45° C. After 35 min, TLC analysis indicated complete conversion of the 2'R, 3'S, 4'S isomer to the 2'R, 3'R, 4'S isomer, and the reaction mixture was then poured into dichloromethane, washed with pH 6 phosphate buffer, dried over MgSO4, and then concentrated under reduced pressure. Chromatography of the residue on silica gel with a 100:0 to 98:2 $CH_2Cl_2$/MeOH gradient afforded 2.0 g (55% from the diazoketone) of the title compound.

Step 9: 1-[2'R,3'R,4'S]-4'-((t-Butyldimethylsilyl)oxymethyl)-3'-hydroxymethyl-2'-oxetanyl)uracil 1-[2'R, 3'R, 4'S]-4'-((t-Butyldimethylsilyl)oxymethyl)-3'-methoxycarbonyl-2'-oxetanyl)uracil (0.595 g, 1.61 mmol), from Step 8, was dissolved in 60mL of absolute ethanol and the ethanol solution was cooled, with stirring under a nitrogen atmosphere, to 0° C. Sodium borohydride (0.6 g) was added and the reaction mixture was stirred for 0.5 h then diluted with 250 mL of methylene chloride. The solution was washed with 100 mL of pH 6 phosphate buffer solution, 100 mL of brine, dried over anhydrous magnesium sulfate, filtered and concentrated under reduced pressure. The residue (0.563 g) was dissolved in 2 mL of methylene chloride and purified by flash chromatography (5-10 psi) on a silica gel column (1×45 cm) eluted with 100 mL of methylene chloride and 100 mL of 5% methanol in methylene chloride to give 0.5 g (92% yield) of the title compound. MS DCI: 343 (M+H)+, 365 (M+Na)+.

Step 10: 1-([2'R,3'R,4'S]-3',4'-Bis(hydroxymethyl)-2'-oxetanyl)uracil

1-[2'R,3'R,4'S]-4'-((t-Butyldimethylsilyl)oxymethyl)-3'-hydroxymethyl-2'oxetanyl)uracil (0.5 g, 1.46 mmol), from Step 9, was dissolved in 10 mL of THF and 0.5 g (1.58 mmol) of tetra-n-butylammonium fluoride was added. The solution was stirred at ambient temperature for 2 h under a nitrogen atmosphere then concentrated under reduced pressure. The residue was dissolved in 50 mL of methylene chloride and 4 mL of 2% glacial acetic acid in methylene chloride was added. The solvent was removed under reduced pressure and the residue purified by flash chromatography (5 psi) on a silica gel column (1×45 cm) eluted with 100 mL of methylene chloride, 100 mL of 5% methanol in methylene chloride and 200 mL of 10% methanol in methylene chloride to give 150 mg (45% yield) of the title compound, $[\alpha]_D^{23}=+61°$ (c, 1.05, $H_2O$). MS DCI: 229 (M+H)+, 246 (M+NH4)+. Analysis calculated for $C_9H_{12}N_2O_5$: C, 47.36; H, 5.30; N, 12.28. Found: C, 47.24; H, 5.29; N, 12.11. $^1$H NMR (D2O, HOD=4.80 ppm) δ3.32 (dddd, 1H, J=7 Hz, J'=j"=J""=6 Hz, CHCHCH), 3.74 (dd, 1H, J=13.5 Hz, J'=4 Hz, OCHCHHOH), 3.86 (dd, 1H, J=13.5 Hz, J'=3 Hz, OCHCHHOH), 3.88 (dd, 1H, J=12.5 Hz, J'=5 Hz, OCHCHCHHOH), 4.69 (ddd, 1H, J=7 Hz, J'=4 Hz, J"=3 Hz, OCHCH2OH), 5.93 (d, 1H, J=8 Hz, NCH=CH), 6.33 (d, 1H, J=6 Hz, OCHN), 8.26 (s, 1H, NCH=CH).

Example 24

1-([2'R,3'R,4'S]-4'-Hydroxymethyl-3'-methyl-2'-oxetanyl)-5-methyl-uracil a) 1-([2'R,3'R,4'S]-4'-((t-Butyldimethylsilyl)oxymethyl)-3'-hydroxymethyl-2'-oxetanyl)-5-methyl-uracil (1.8 g) the product of step 7 of Example 21, is dissolved in 8 mL of methylene chloride under a nitrogen atmosphere. The solution is cooled to 0° C. and 1.1 g of triethylamine and 0.69 g of methanesulfonyl chloride are added. The reaction mixture is allowed to warm to ambient temperature and stirred at ambient temperature for approximately 2 h. The reaction mixture is diluted with ethyl acetate, washed with saturated aqueous sodium bicarbonate and brine, dried over anhydrous sodium sulfate and concentrated under reduced pressure to give 1-[2'R,3'R,4'S]-4'-((t-butyldimethylsilyl)oxymethyl)-3'-methanesulfonyloxymethyl-2'-oxetanyl)-5-methyl-uracil.

b) 1-[2'R,3'R,4'S]-4'-((t-buyldimethylsilyl)oxymethyl)-3'-methanesulfonyloxymethyl-2'-oxetanyl)-5-methyl-uracil (0.44 g) is dissolved in 0.5 mL of THF under a nitrogen atmosphere. Lithium triethylborohydride (1.2 mL of a 1M solution) is added to the solution of the nucleoside, with stirring, at 0° C. The reaction mixture is allowed to warm to ambient temperature and stirred at ambient temperature for 4 h then partitioned between ethyl acetate and saturated aqueous sodium bicarbonate. The layers are separated and the organic phase is washed with brine, dried over anhydrous sodium sulfate and concentrated under reduced pressure. The residue is purified by column chromatography to afford 1-([2'R,3'R,4'S]-4'-((t-butyldimethylsilyl)oxymethyl)-3'-methyl-2'-oxetanyl)-5-methyl-uracil.

c) 1-([2'R,3'R,4'S]-4'-((t-butyldimethylsilyl)oxymethyl)-3'-methyl-2'-oxetanyl)-5-methyl-uracil is deprotected as described in Step 8 of Example 21 to give the title compound.

Example 25

1-([2'R,3'R,4'S]-3'-Fluoromethyl-4'-hydroxymethyl-2'-oxetanyl)-5-methyl-uracil

The procedures of Example 24(a) can be repeated to obtain 1-([2'R, 3'R, 4'S]4'-((t-butyldimethylsilyl)oxymethyl)-3'-methanesulfonyloxymethyl-2'-oxetanyl)-5-methyl-uracil. 1-([2'R, 3'R, 4'S]4'-((t-Butyldimethylsilyl)oxymethyl)-3'-methanesulfonyloxymethyl-2'-oxetanyl)-5-methyl-uracil (0.44 g) is combined with 8 mL of a 1M solution of n-butylammonium fluoride in THF under a nitrogen atmosphere. The reaction mixture is heated at reflux temperature for 4 h then cooled to ambient temperature and concentrated under reduced pressure. Purification by chromatography on silica gel eluting With MeOH/$CH_2Cl_2$ affords the desired compound.

Example 26

1-([2'R, 3'R, 4'S]-4'-Hydroxymethyl-3'-iodomethyl-2'-oxetanyl)-5-methyl-uracil a) The procedures of Example 25 can be repeated, replacing n-butylammonium fluoride with n-butylammonium iodide, to obtain 1-([2'R, 3'R, 4'S] 4-((t-butyldimethylsilyl)oxymethyl)-3'-iodomethyl-2'-oxetanyl)-5-methyl-uracil.

b) The procedure of Step 8 of Example 21 can be repeated replacing 1-([2'R, 3'R, 4'S]-4'-((t-butyldimethylsily)oxymethyl)-3'-hydroxymethyl-2'-oxetanyl)-5-methyl-uracil with the material obtained from Example 26(a) to obtain the desired compound.

Example 27

1-([2'R, 3'R, 4'S-3'-Azidomethyl-4'-hydroxymethyl-2'-oxetanyl)-5-methyl-uracil

The procedures of Example 26 can be repeated, replacing n-butylammonium iodide with n-butylammonium azide, to obtain the desired compound.

Example 28

1-([2'R,3'R,4'S]-3'-Aminomethyl-4'-hydroxymethyl-2'-oxetanyl)-5-methyl-uracil a) The procedure of Example 27 can be repeated to obtain 1-([2'R, 3'R, 4'S]-3'-azidomethyl-4'-hydroxymethyl-2'-oxetanyl)-5-methyl-uracil.

b) 1-([2'R, 3'R, 4'S]-3'-Azidomethyl-4'-hydroxymethyl-2'-oxetanyl)-5-methyl-uracil (0.28 g) is dissolved in 10 mL of methanol and the methanol solution flushed with nitrogen. The catalyst (2 g of 5% palladium on carbon) is added and the reaction mixture placed under an atmosphere of hydrogen and stirred at ambient temperature for 1 h. The catalyst is removed by filtration through Celite filter aid and rinsed well with methanol. The filtrate is concentrated under reduced pressure to afford the desired compound.

Example 29

1-([2'R, 3'R, 4'S]-3'-Chloromethyl-4'-hydroxymethyl-2'-oxetanyl)-5-methyl-uracil The procedures of Example 26 can be repeated, replacing n-butylammonium iodide with lithium chloride in THF and 2-butanone, to obtain the desired compound.

Example 30

1-([2'R, 3'R, 4'S]-4'-Hydroxymethyl-3'-methyl-2'-oxetanyl)uracil a) 1-([2'R, 3'R, 4'S]-4'-((t-Butyldimethylsilyl)oxymethyl)-3'-hydroxymethyl-2'-oxetanyl)uracil (1.8 g) the product of step 9 of Example 23, is dissolved in 8 mL of methylene chloride under a nitrogen atmosphere. The solution is cooled to 0° C. and 1.1 g of triethylamine and 0.69 g of methanesulfonyl chloride are added. The reaction mixture is allowed to warm to ambient temperature and stirred at ambient temperature for approximately 2 h. The reaction mixture is diluted with ethyl acetate, washed with saturated aqueous sodium bicarbonate and brine, dried over anhydrous sodium sulfate and concentrated under reduced pressure to give 1-[2'R, 3'R, 4'S]-4'-((t-butyldimethylsilyl)oxymethyl)-3'-methanesulfonyloxymethyl-2'-oxetanyl)uracil.

b) 1-([2'R, 3'R, 4'S]-4'-((t-Butyldimethylsilyl)oxymethyl)-3'-methanesulfonyloxymethyl-2'-oxetanyl)uracil (0.44 g) is dissolved in 0.5 mL of THF under a nitrogen atmosphere. Lithium triethylborohydride (1.2 mL of a 1M solution) is added to the solution of the nucleoside, with stirring, at 0° C. The reaction mixture is allowed to warm to ambient temperature and stirred at ambient temperature for 4 h then partitioned between ethyl acetate and saturated sodium bicarbonate. The layers are separated and the organic phase is washed with brine, dried over anhydrous sodium sulfate and concentrated under reduced pressure. The residue is purified by column chromatography to afford 1-([2'R, 3'R, 4'S]-4'-((t-butyldimethylsilyl)oxymethyl)-3'-methyl-2'-oxetanyl)uracil.

c) 1-([2'R, 3'R, 4'S]-4'-((t-Butyldimethylsilyl)oxymethyl)-3'-methyl-2'oxetanyl)uracil is deprotected as described in Step 8 of Example 21 to give the title compound.

Example 31

1-((2'R,3'R,4'S)-3'-Fluoromethyl-4'-hydroxymethyl-2'-oxetanyl)uracil

The procedures of Example 30(a) can be repeated to obtain 1-([2'R, 3'R, 4'S]-4'-((t-butyldimethylsilyl)oxymethyl)-3'-methanesulfonyloxymethyl-2'-oxetanyl)uracil. 1-([2'R, 3'R, 4'S]-4'-((t-Butyldimethylsilyl)oxymethyl)-3'-methanesulfonyloxymethyl-2'-oxetanyl)uracil (0.44 g) is combined with 8 mL of a 1M solution of n-butylammonium fluoride in THF under a nitrogen atmosphere. The reaction mixture is heated at reflux temperature for 4 h then cooled to ambient temperature and concentrated under reduced pressure. Purification by chromatography on silica gel eluting with MeOH/CH$_2$Cl$_2$ affords the desired compound.

Example 32

1([2'R, 3'R, 4'S]-4'-Hydroxymethyl-3'-iodomethyl-2'-oxetanyl)uracil a) The procedures of Example 31 can be repeated, replacing n-butylammonium fluoride with n-butylammonium iodide, to obtain 1-([2'R, 3'R, 4'S] 4'-((t-butyldimethylsilyl)oxymethyl)-3'-iodomethyl-2'oxetanyl)uracil.

b) The procedure of Step 8 of Example 21 can be repeated replacing 1-([2'R, 3'R, 4'S]-4'-((t-butyldimethylsilyl)oxymethyl)-3'-hydroxymethyl-2'-oxetanyl)-5-methyl-uracil with the material obtained from Example 32(a) to obtain the desired compound.

Example 33

1([2'R, 3'R, 4'S]-3'-Azidomethyl-4'-hydroxymethyl-2'-oxetanyl)uracil a) The procedures of Example 32 can be repeated, replacing n-butylammonium iodide with n-butylammonium azide, to obtain the desired compound.

Example 34

1-([2'R, 3'R, 4'S]-3'-Aminomethyl-4'-hydroxymethyl-2'-oxetanyl)uracil a) The procedure of Example 33 can be repeated to obtain 1-([2'R, 3'R, 4'S]-3'-azidomethyl-4'-hydroxymethyl-2'-oxetanyl)uracil b) 1-([2'R, 3'R, 4'S) 3'-Azidomethyl-4'-hydroxymethyl-2'-oxetanyl)uracil (0.28 g) is dissolved in 10 mL of methanol and the methanol solution flushed with nitrogen. The catalyst (2g of 5% palladium on carbon) is added and the reaction mixture placed under an atmosphere of hydrogen and stirred at ambient temperature for 1 h. The catalyst is removed by filtration through Celite filter aid and rinsed well with methanol. The filtrate is concentrated under reduced pressure to afford the desired compound.

Example 35

1-([2'R, 3'R, 4'S]-3'-Chloromethyl-4'-hydroxymethyl-2'-oxetanyl)uracil

The procedures of Example 32 can be repeated, replacing n-butylammonium iodide with lithium chloride in THF and 2-butanone, to obtain the desired compound.

Example 36

1-([2'R, 3'R, 4'S]-4'-Hydroxymethyl-3'-methyl-2'-oxetanyl)cytosine a) 1-([2'R, 3'R, 4'S]-4'-((t-Butyldimethylsilyl)oxymethyl)-3'-hydroxymethyl-2'-oxetanyl)cytosine (1.8 g) the product of step 8 of Example 22, is dissolved in 8 mL of methylene chloride under a nitrogen atmosphere. The solution is cooled to 0° C. and 1.1 g of triethylamine and 0.69 g of methanesulfonyl chloride are added. The reaction mixture is allowed to warm to ambient temperature and stirred at ambient temperature for approximately 2 h. The reaction mixture is diluted with ethyl acetate, washed with saturated aqueous sodium bicarbonate and brine, dried over anhydrous sodium sulfate and concentrated under reduced pressure to give 1-([2'R, 3'R, 4'S]-4'-((t-butyldimethylsilyl)oxymethyl)-3'-(methanesulfonyloxy)methyl-2'-oxetanyl)-cytosine.

b) 1-([2'R, 3'R, 4'S]-4'-((t-butyldimethylsilyl)oxymethyl)-3'-methanesulfonyloxymethyl-2'-oxetanyl)-cytosine (0.44 g) is dissolved in 0.5 mL of THF under a nitrogen atmosphere. Lithium triethylborohydride ( 1.2 mL of a 1M solution) is added to the solution of the nucleoside, with stirring, at 0° C. The reaction mixture is allowed to warm to ambient temperature and stirred at ambient temperature for 4 h then partitioned between ethyl acetate and saturated sodium bicarbonate. The layers are separated and the organic phase is washed with brine, dried over anhydrous sodium sulfate and concentrated under reduced pressure. The residue is purified by column chromatography to afford 1-([2'R, 3'R, 4'S]-4'-((t-butyldimethylsilyl)oxymethyl)-3'-methyl-2'-oxetanyl)cytosine.

c) 1-([2'R, 3'R, 4'S]-4'-((t-butyldimethylsilyl)oxymethyl)-3'-methyl-2'-oxetanyl)cytosine is deprotected as described in Step 8 of Example 21 to give the title compound.

Example 37

1-([2'R, 3'R, 4'S]-3'-Fluoromethyl-4'-hydroxymethyl-2'-oxetanyl)cytosine

The procedures of Example 36(a) can be repeated to obtain 1-((2'R,3'R,4'S) 4'-((t-butyldimethylsilyl)oxymethyl)-3'-methanesulfonyloxymethyl-2,-oxetanyl)cytosine. 1-([2'R, 3'R, 4'] 4'-((t-Butyldimethylsilyl)oxymethyl)-3'-methanesulfonyloxymethyl-2'-oxetanyl)cytosine (0.44 g) is combined with 8 mL of a 1M solution of n-butylammonium fluoride in THF under a nitrogen atmosphere. The reaction mixture is heated at reflux temperature for 4 h then cooled to ambient temperature and concentrated under reduced pressure. Purification by chromatography on silica gel eluting with MeOH/CH$_2$Cl$_2$ affords the desired compound.

Example 38

1-([2'R, 3'R, 4'S]-4'-Hydroxymethyl-3'-iodomethyl-2'-oxetanyl)cytosine

The procedures of Example 37 can be repeated, replacing n-butylammonium fluoride with n-butylammonium iodide, to obtain 1-([2'R, 3'R, 4'S] 4'-((t-butyldimethylsilyl)oxymethyl)-3'-iodomethyl-2'-oxetanyl)-cytosine.

b) The procedure of Step 8 of Example 21 can be repeated replacing 1-([2'R, 3'R, 4'S]-4'-((t-butyldimethylsilyl)oxymethyl)-3'-hydroxymethyl-2'-oxetanyl)-5-methyl-uracil with the material obtained from Example 38(a) to obtain the desired compound.

Example 39

1-[2'R, 3'R, 4'S]-3'-Azidomethyl-4'-hydroxymethyl-2'-oxetanyl)cytosine

The procedures of Example 38 can be repeated, replacing n-butylammonium iodide with n-butylammonium azide, to obtain the desired compound.

Example 40

1-([2'R, 3'R, 4'S]-3'-Aminomethyl-4'-hydroxymethyl-2'-oxetanyl)cytosine a) The procedure of Example 39 can be repeated to obtain 1-([2'R, 3'R, 4'S]-3'-azidomethyl-4'-hydroxymethyl-2'-oxetanyl)cytosine.

b) 1-([2'R, 3'R, 4'S]-3'-Azidomethyl-4'-hydroxymethyl-2'-oxetanyl)cytosine (0.28 g) is dissolved in 10 mL of methanol and the methanol solution flushed with nitrogen. The catalyst (2g of 5% palladium on carbon) is added and the reaction mixture placed under an atmosphere of hydrogen and stirred at ambient temperature for 1 h. The catalyst is removed by filtration through Celite filter aid and rinsed well with methanol. The filtrate is concentrated under reduced pressure to afford the desired compound.

Example 41

1-([2'R, 3'R, 4'S]-3'-Chloromethyl-4,-hydroxymethyl-2'-oxetanyl)cytosine

The procedures of Example 38 can be repeated, replacing n-butylammonium iodide with lithium chloride in THF and 2-butanone, to obtain the desired compound.

Example 42

1-([2'R, 3'R, 4'S]-3',4'-Bis(hydroxymethyl)-2'-oxetanyl)-5-iodouracil

To a stirred solution of 413 mg (1.81 mmol) of 1-([2'R, 3'R, 4'S]-3',4'-bis(hydroxymethyl)-2'-oxetanyl)uracil, the product of Step 10 of Example 23, in 16.5 mL of anhydrous DMF were added 1.05 g (5.16 mmol) of 2,6-di-t-butyl pyridine followed by 556 mg (3.43 mmol) of ICl in 8.3 mL of DMF. After 4 h at room temperature, 1.26 mL (9.1 mmol) of triethylamine were added and the reaction mixture was concentrated under reduced pressure. Chromatography of the residue on C18 Bondesil with a 100:0 to 80:20 H$_2$O/MeOH gradient afforded 355 mg (55%) of the title compound as an amorphous white solid: $^1$H NMR (DMSO, TMS=0.00 ppm) δ3.0–3.8 (m, 5H), 4.47 (ddd, 1H, J=7 Hz, J'=J''=2 Hz), 4.93 (dd, 1H, J=J'=5 Hz), 5.48 (dd, 1H, J=J'=5 Hz), 6.22 (d, 1H, J=6 Hz), 8.96 (s, 1H); FAB MS m/z 355 (M +H)+.

Example 43

1-([2'R, 3'R, 4'S]-3',4'-Bis(hydroxymethyl)-2'-oxetanyl)-5-bromouracil

Step 1: 1-[2'R, 3'R, 4'S]-4'-((t-Butyldimethylsily)oxymethyl)-3'-hydroxymethyl -2'-oxetanyl)-5-bromouracil To a stirred solution of 100 mg (0.29 mmol) of 1-[2'R, 3'R, 4'S]-4'-((t-Butyldimethylsilyl)oxymethyl)-3'-hydroxymethyl-2'-oxetanyl)uracil, the product of Step 9 of Example 23, in 1 mL of pyridine were added 440 uL (0.44 mmol) of a 1.0M solution of Br$_2$ in CCl$_4$. After 1 h at room temperature, the reaction mixture was diluted with 100 mL of CH$_2$Cl$_2$, washed sequentially with 50 mL of pH 6 phosphate buffer, 50 mL of 5% aqueous NaHCO$_3$, and 50 mL of saturated aqueous NaCl, dried over MgSO$_4$, and then concentrated under reduced pressure to afford a nearly quantitative yield of the desired product: $^1$H NMR (CDCl$_3$, TMS=0.00 ppm) δ0.14, 0.16 (2 s, 6H), 0.93 (s, 9H), 3.28 (dddd, 1H), 3.65 (dd, 1H), 3.86 (dd, 1H), 3.92 (dd, 1H), 4.00 (dd, 1H), 4.67 (ddd, 1H), 6.18 (d, 1H), 8.39 (s, 1H), 9.68 (bs, 1H); DCI NH$_3$ MS m/z 421, 423 (M+H)+, 438 440 (M+NH$_4$)+.

Step 2: 1-([2'R, 3'R, 4'S]-3',4'-Bis(hydroxymethyl)-2'-oxetanyl)-5-bromouracil

To a stirred solution of 132 mg (0.31 mmol) of 1-[2'R, 3'R, 4'S]-4'-((t-butyldimethylsilyl)oxymethyl)-3'-hydroxymethyl-2'-oxetanyl)-5-bromouracil, the product of Step 1 of Example 43, in 2 mL of THF were added 100 mg (0.32 mmol) of tetra-n-butylammonium fluoride trihydrate. After 6.5 h at room temperature, the reaction mixture was cooled to 5° C., and after 16 h at this temperature, allowed to warm to room temperature. The reaction mixture was then concentrated under reduced pressure, redissolved in 0.85 mL of CH$_2$Cl$_2$ containing 0.32 mmol of glacial HOAc, and then concentrated under reduced pressure. Chromatography of the residue on silica gel with a 100:0 to 9:1 CH$_2$Cl$_2$/MeOH gradient followed by further purification by chromatography on C18 Bondesil with a 100:0 to 96:4 H$_2$O/MeOH gradient afforded 45 mg (47%) of the title compound as an amorphous white solid: $^1$H NMR (DMSO, TMS=0.00 ppm) δ3.15–3.75 (m, 5H), 4.48 (ddd, 1H), 4.95 (dd, 1H), 5.50 (dd, 1H), 6.24 (d, 1H), 8.94 (s, 1H) ; DCI NH$_3$ MS m/z 324, 326 (M+NH$_4$)+.

ALTERNATE PROCEDURE

To a stirred solution of 5 mg (0.022 mmol) of 1-([2'R, 3'R, 4'S]-3',4'-bis(hydroxymethyl)-2'-oxetanyl)uracil, the product of Step 10 of Example 23, in 0.10 mL of pyridine was added 5.3 mg (0.033 mmol) of bromine in 18 uL of CCl$_4$. After 1 h at room temperature, 11.1 mg (0.111 mmol) of triethylamine were added and the reaction mixture was concentrated under reduced pressure. Chromatography of the residue on silica gel with a 100:0 to 90:10 gradient of CH$_2$Cl$_2$—/MeOH afforded 0.8 mg (12%) of the title compound as an amorphous white solid: $^1$H NMR (D$_2$O, TSP=0.00 ppm) δ3.33 (m, 1H), 3.76 (dd, 1H, J=14 Hz, J'=3 Hz), 3.8–3.95 (m, 2H), 3.90 (dd, 1H, J=14 Hz, J'=2 Hz), 6.32 (d, 1H, J=6 Hz), 8.71 (s, 1H); DCI NH$_3$ MS m/z 324, 326 (M+NH$_4$)+.

Example 44

1-([2'R, 3'R, 4'S]-3',4'-Bis(hydroxymethyl)-2'-oxetanyl)-5-(2-bromo-1-vinyl)uracil Step 1: 1-([2'R, 3'R, 4'S]-3',4'-Bis(hydroxymethyl)-2'-oxetanyl)-5-(2-(trimethylsilyl)-1-vinyl)uracil To a stirred solution of 170 mg (0.48 mmol) of 1-([2'R, 3'R, 4'S]-3',4'-bis(hydroxymethyl)-2'-oxetanyl)-5-iodouracil, the product of Example 42, in 2 mL of DMF were added 334 mg (0.86 mmol) of 1-(2-(trimethylsilyl)-vinyl)tri-n-butylstannane and 34 mg (0.048 mmol) of bis (triphenylphosphine)palladium(II) chloride. The resulting mixture was heated under a N$_2$ atmosphere for 1.75 h at 60° C., cooled to room temperature, and then diluted with 200 mL of MeOH which had been saturated with hexane. The MeOH phase was then washed with 4×40 mL of hexane, filtered, and then concentrated under reduced pressure. Chromatography of the residue on silica gel with a 97.5:2.5 to 90:10/CH$_2$Cl$_2$:MeOH gradient afforded 99.9 mg (64%) of the title compound: $^1$H NMR (CDCl$_3$, TMS=0.00 ppm) δ0.12 (s, 9H), 3.36 (dddd, 1H), 3.59–3.98 (m, 4H), 4.59 (m, 1H), 6.39 (d, 1H), 6.58 (d, 1H), 6.73 (d, 1H), 8.81 (s, 1H); DCI NH$_3$ MS, m/z 327 (M+H)+.

Step 2: 1-([2'R, 3'R, 4'S]-3',4'-Bis(hydroxymethyl)-2'-oxetanyl)-5-(2-bromo-1-vinyl)uracil To a stirred solution of 95 mg (0.29 mmol) of 1-([2'R, 3'R, 4'S]-3',4'-Bis(hydroxymethyl)-2'-oxetanyl)-5-(2-(trimethylsilyl)-1-vinyl)uracil, the product of Step 1 of Example 44 in 5.4 mL of DMF at −30° C. were added 535 uL of MeOH, 80 uL (0.58 mmol) of triethylamine, and then dropwise, 347 uL (0.347 mmol) of a 1M solution of bromine in carbon tetrachloride. The reaction mixture was then allowed to warm to room temperature and then concentrated under reduced pressure. Chromatography of the residue on C18 Bondesil with a 100:0 to 70:30 H$_2$O/MeOH gradient afforded 72 mg (74%) of the title compound as an amorphous white solid: $^1$H NMR (DMSO, TMS=0.00 ppm) δ3.13–3.78 (m, 5H), 4.49 (m, 1H), 4.96 (dd, 1H), 5.36 (dd, 1H), 6.24 (d, 1H), 6.85 (d, 1H), 7.24 (d, 1H), 8.58 (s, 1H), 11.51 (bs, 1H); DCI NH$_3$ MS, m/z 350, 352 (M+NH$_4$)+.

Example 45

1-([2'R, 3'R, 4'S]-3',4'-Bis(hydroxymethyl)-2'-oxetanyl)-5-chlorouracil

This procedure of Example 21 by substituting 5-chlorouracil for 5-methyluracil in the procedure of M. Saneyoshi, et al Chem Pharm Bull, 30, 2237-1982 This provides 2',5'-bis-(O-(4''-chloro)benzoyl)-5-chloro-3'-deoxyuridine, which is substituted for 2',5'-bis-(O-(4''-chloro)benzoyl)-5-methyl-3'-deoxyuridine in the procedures of Example 21.

Example 46

1-([2'R, 3'R, 4'S]-3',4'-Bis(hydroxymethyl)-2'-oxetanyl)-5-fluorouracil

This procedure of Example 21 by substituting 5-fluorouracil for 5-methyluracil in the procedure of M. Saneyoshi, et al Chem Pharm Bull, 30, 2237-1982. This provides 2',5'-bis-(O-(4''-chloro)benzoyl)-5-fluoro-3'-deoxyuridine, which is substituted for 2',5'-bis-(O-(4''-chloro)benzoyl)-5-methyl-3'-deoxyuridine in the procedures of Example 21.

Example 47

1-([2'R, 3'R, 4'S]-3',4'-Bis(hydroxymethyl)-2'-oxetanyl)-5-(trifluoromethyl)uracil This compound is synthesized according to the procedure of Example 21 by substituting 5-(trifluoromethyl)uracil for 5-methyluracil in the procedure of M. Saneyoshi, et al Chem Pharm Bull, 30, 2237-1982 This provides 2',5'-bis-(O-(4"-chloro)benzoyl)-5-trifluoromethyl-3'-deoxyuridine, which is substituted for 2',5'-bis-(O-(4"-chloro)benzoyl)-5-methyl-3'-deoxyuridine in the procedures of Example 21.

Example 48

1-([2'R, 3'R, 4'S]-3',4'-Bis(hydroxymethyl)-2'-oxetanyl)-5-ethyluracil

To a stirred solution of 38 mg (0.15 mmol) of 1-([2'R, 3'R, 4'S]-3',4'-Bis(hydroxymethyl)-2'-oxetanyl)-5-vinyluracil, the product of Example 61, in 1.7 mL of pyridine was added 13 mg of 5% Pd-BaSO4 and the resulting mixture was stirred under 1 atmosphere of hydrogen for 18 h, filtered, and then concentrated under reduced pressure. To a stirred solution of 37 mg (0.15 mmol) of the residue in 2 mL of methanol was added 30 mg (0.30 mmol) of triethylamine and 20 mg of 10% Pd—C, and the resulting mixture was stirred under 1 atmosphere of hydrogen for 18 h, filtered and then concentrated under reduced pressure. Chromatography of the residue on C18 Bondesil with a 100:0 to 50:50 gradient of water/MeOH afforded the title compound: $^1$H NMR (DMSO, TMS=0.00 ppm) $\delta$1.07 (t, 3H), 2.23 (q, 2H), 3.0–3.8 (m, 5H), 4.41 (m, 1H), 4.92 (dd, 1H), 5.38 (dd, 1H), 6.30 (d, 1H), 8.33 (s, 1H), 11.29 (bs, 1H); FAB MS, m/z 257 (M+H)+.

Example 49

1([2'R, 3'R, 4'S]-3',4'-Bis(hydroxymethyl)-2'-oxetanyl)-5-(2-iodo-1-vinyl)uracil Step 1: 1-[2'R,3'R,4'S]-440-((t-Butyldimethylsilyl)oxymethyl)-3'-hydroxymethyl-2'-oxetanyl)-5-iodouracil To a stirred solution of 7.45 g (21.6 mmol) of 1-[2'R, 3'R, 4'S]-4'-((t-Butyldimethylsilyl)oxymethyl)-3'-hydroxymethyl-2'-oxetanyl)uracil, the product of Step 9 of Example 23, in 200 mL of DMF were added 11 g (54.3 mmol) of 2,6-di-t-butyl-4-methylpyridine and 109 mL of a 1.0M solution of ICl in DMF. After ¾ hour at ambient temperature, the reaction mixture was diluted with 700 mL Et$_2$O and washed with 500 mL 5% NaHCO$_3$ plus 10 g sodium bisulfite. The aqueous phase was further extracted with Et$_2$O (2×250 mL). The Et$_2$O extracts were combined, washed with 700 mL saturated aqueous NaCl, dried over MgSO$_4$, and then concentrated under reduced pressure. Chromatography of the residue on silica gel with a 100:1 to 97:3 CH$_2$Cl$_2$/MeOH gradient afforded 6.3 g (63%) of the title compound as an amorphous white solid: $^1$H NMR (CDCl$_3$, TMS=0.00 ppm) $\delta$0.14 (s, 3H), 0.15 (S, 3H), 0.93 (s, 9H), 3.24 (m, 1H), 3.63 (dd, 1H), 3.83 (dd, 1H), 3.97 (m, 2H), 4.64 (dt, 1H), 6.07 (d, 1H), 8.37 (s, 1H), 8.88 (s, 1H); DCI NH$_3$ MS, m/z 486 (M+NH$_4$)+.

Step 2: 1-([2'R,3'R,4'S]-4'-((t-Butyldimethylsilyl)oxymethyl)-3'-hydroxymethyl-2'-oxetanyl)-5-(2-trimethylsilyl)-1-vinyl)uracil To a stirred solution of 6.33 g (13.5 mmol) of 1-([2'R, 3'R, 4'S]-4'-((t-butyldimethysilyl)oxymethyl)-3'-hydroxymethyl-2'-oxetanyl)-5-iodouracil, the product of Step 1 of Example 49, in 63 mL of DMF were added 6.3 g (16.2 mmol) of 1-(2-(trimethylsilyl)vinyl)-tri-n-butylstannane, 310 mg (1.34 mmol) of tri-(2-furyl)phosphine and 171 mg (0.66 mmol) of bis(triphinylphosphine)palladium (II) chloride. The resulting mixture was heated under a N$_2$ atmosphere at 50° for 26 hours. 2.75 g (13.5 mmol) of iodobenzene was added and heating was continued at 50° for 3 hours. The reaction mixture was diluted with 600 mL EtOAc and washed with 600 mL of 0.5M NaF, dried over MgSO$_4$, and then concentrated under reduced pressure. Chromatography of the residue on silica gel with a 99:1 to 98.5:1.5 CH$_2$Cl$_2$/MeOH gradient afforded 3.2 g (54%) of the title compound as an amorphous white solid: $^1$H NMR (CDCl$_3$, TMS=0.00 ppm) $\delta$0.07 (s, 3H), 0.12 (s, 6H), 0.89 (s, 9H), 3.20 (m, 1H), 3.65 (dd, 1H), 3.81 (dd, 1H), 3.99 (m, 2H), 4.62 (m, 1H), 6.02 (d, 1H), 6.65 (s, 2H), 8.01 (s, 1H), 8.50 (s, 1H); DCI NH$_3$ MS, m/z 441 (M+H)+.

Step 3: 1-([2'R,3'R,4'S]-4'-((t-Butyldimethylsilyl)oxymethyl)-3'hydroxymethyl-2'-oxetanyl)-5-(2-iodo-1-vinyl)uracil To a stirred solution of 300 mg (0.68 mmol) of 1-([2'R, 3'R, 4'S]-4'-((t-Butyldimethylsilyl)oxymethyl)-3'-hydroxymethyl-2'-oxetanyl)-5-(2-trimethylsilyl)-1vinyl)uracil, the product of Step 2 of Example 49, in 18 mL DMF were added 237 mg (1.16 mmol) of 2,6-di-t-butyl-4-methylpyridine and 1.5 mL of a 1.0M solution of ICl in DMF. After 3 hours at ambient temperature, the reaction mixture was diluted with 100 mL Et$_2$O and washed with 100 mL 5% NaHCO$_3$ plus 420 mg sodium bisulfite. The aqueous phase was extracted with 100 mL Et$_2$O. The Et$_2$O extracts were combined, dried over MgSO$_4$ and then concentrated under reduced pressure. Chromatography of the residue on silica gel with a 98.5:1.5 CH$_2$Cl$_2$/MeOH gradient afforded 104 mg (31%) of the title compound as an amorphous white solid: $^1$H NMR (CDCl$_3$, TMS=0.00 ppm) $\delta$0.09 (s, 3H), 1.01 (s, 3H), 0.91 (s, 9H), 3.21 (m, 1H), 3.64 (dd, 1H), 3.82 (dd, 1H), 3.98 (m, 2H), 4.62 (m, 1H), 6.08 (d, 1H), 7.05 (d, 1H, J=5Hz), 7.41 (d, 1H, J=5Hz), 7.99 (s, 1H), 8.44 (s, 1H); DCI NH$_3$ MS, m/z 495 (M+H)+.

Step 4: 1-([2'R,3'R,4'R]3',4'-Bis(hydroxymethyl)-2-oxetanyl)-5-(2-iodo-1-vinyl)uracil To a stirred solution of 206 mg (0.42 mmol) of 1-([2'R, 3'R, 4'S]-4'-((t-Butyldimethylsilyl)oxymethyl)-3'-hydroxymethyl-2'-oxetanyl)-5-(2-iodo-1-vinyl) uracil, the product of Step 3 of Example 49, in 2 mL THF was added 145 mg (0.46 mmol) of tetra-n-butylammonium fluoride trihydrate. The mixture was stirred at ambient temperature for 3.5 hours and 24 µL of glacial acetic acid was added. The resultant solution was concentrated under reduced pressure. The residue was taken up in 6 mL of 1:1 MeOH/H$_2$O and the organic solvent removed under reduced pressure at 50°. Cool the resulting aqueous mixture to 0° and harvest 114 mg (72%) of the title compound as white crystals: Analysis calculated for C$_{11}$H$_{13}$IN$_2$O$_5$: C, 34.75; H, 3.45; N, 7.37. Found: C, 35.00; H, 3.42; N, 7.33; $^1$H NMR (DMSO-D$_6$, TMS=0.00 ppm) $\delta$3.15–3.75 (m, 6H), 4.49 (m, 1H), 4.95 (t, 1H), 5.38 (t, 1H), 6.24 (d, 1H), 7.17 (dd, 2H), 8.60 (s, 1H); DCI NH$_3$ MS, m/z 381 (M+H)+.

Example 50

1-([2'R, 3'R, 4'S]-3',4'-Bis(hydroxymethyl)-2'-oxetanyl)-5-(2-chloro-1-vinyl)uracil Step 1: ([2'R,3'R,4'S]-4'-((t-Butyldimethylsilyl)oxymethyl)-3'-hydroxymethyl-2'-oxetanyl)-5-(2-chloro-1-vinyl)uracil To a stirred solution of 250 mg (0.57 mmol) 1-([2'R, 3'R, 4'S]-4'-((t-Butyldimethylsilyl)oxymethyl)-3'-hydroxymethyl-2'-oxetanyl)-5-(2-trimethylsilyl)-1-vinyl)uracil, the product of Step 2 of Example 49, in 11 mL of 10:1 DMF/MeOH was added 188 µL (1.38 mmol) of triethylamine. The mixture was cooled to −30° and treated with 53 mg (0.23 mmol) of trichloroisocyanuric acid. After 15 minutes, the reaction mixture was concentrated at reduced pressure and purified by chromatography on silica gel with 98.5:1.5 $CH_2Cl_2$/MeOH to afford 178 mg (77%) of the title compound as an amorphous white solid: $^1$H NMR ($CDCl_3$, TMS=0.00 ppm) δ0.08 (s, 3H), 0.11 (s, 3H), 0.92 (s, 9H), 3.22 (m, 1H), 3.64 (dd, 1H), 3.83 (dd, 1H), 3.98 (m, 2H), 4.12 (m, 1H), 6.08 (d, 1H), 6.43 (d, 1H, J=4Hz), 7.31 (d, 1H, J=4Hz), 7.96 (s, 1H), 8.50 (s, 1H); DCI $NH_3$ MS, m/z 403 (M+H)+.

Step 2: 1-([2′R,3′R,4′S]3′,4′-Bis(hydroxymethyl)-2′-oxetanyl)-5-(2-chloro-1-vinyl)uracil To a stirred solution of 195 mg (0.48 mmol) of 1-([2′R, 3′R, 4′S]-4′-((t-Butyldimethylsilyl)oxymethyl)-3′-hydroxymethyl-2′-oxetanyl)-5-(2-chloro-1-vinyl)uracil, the product of Step 1 of Example 50, in 2 mL THF was added 168 mg (0.53 mmol) of tetra-n-butylammonium fluoride trihydrate. The mixture was stirred at ambient temperature for 2 hours and 28 μL of glacial acetic acid was added. The resultant solution was concentrated under reduced pressure. The residue was taken up in 1:1 MeOH/$H_2O$ (6 mL) and the organic solvent removed under reduced pressure at 50°. Cool the resulting aqueous mixture to 0° and harvest 106 mg (76%) of the title compound as white crystals: Analysis calculated for $C_{11}H_{13}ClN_2O_5$: C, 45.76; H, 4.54; N, 9.71. Found: C, 45.62; H, 4.63; N, 9.50; $^1$H NMR (DMSO-$D_6$, TMS 0.00 ppm) δ3.13–3.75 (m, 6H), 4.49 (m, 1H), 4.95 (t, 1H), 5.35 (t, 1H), 6.24 (d, 1H), 6.59 (d, 1H, J=4 Hz), 7.17 (d, 1H, J=4 Hz), 8.57 (s, 1H); DCI $NH_3$ MS, m/z 289.291 (M+H)+.

Example 51

1-([2′R, 3′R, 4′S]-3′,4′-Bis(hydroxymethyl)-2′-oxetanyl)-5-bromocytosine

This compound is prepared in analogy to the alternate procedure for Example 43, but substituting 1-([2′R, 3′R, 4′S]-3′,4′-bis(hydroxymethyl)-2′-oxetanyl)cytosine for 1-([2′R, 3′R, 4′S]-3′, 4′-Bis(hydroxymethyl)-2′-oxetanyl)uracil.

Example 52

1-([2′R, 3′R, 4′S]-3′,4′-Bis(hydroxymethyl)-2′-oxetanyl)-5-iodocytosine

This compound is prepared in analogy to the procedure for Example 42, but substituting 1-([2′R, 3′R, 4′S]-3′,4′-bis(hydroxymethyl)-2′-oxetanyl)cytosine for 1-([2′R, 3′R, 4′S]-3′,4′-Bis(hydroxymethyl)-2′-oxetanyl)uracil.

Example 53

1-([2′R, 3′R, 4′S]-3′,4′-Bis(hydroxymethyl)-2′-oxetanyl)-5-(trans-2-bromo-1-vinyl)cytosine This compound is prepared in analogy to the procedure for Example 44, but substituting 1-([2′R, 3′R, 4′S]-3′,4′-Bis(hydroxymethyl)-2′-oxetanyl)-5-iodocytosine for 1-([2′R, 3′R, 4′S]-3′,4′-Bis(hydroxymethyl)-2′-oxetanyl)-5-iodouracil.

Example 54

1-([2′R, 3′R, 4′S]-3′,4′-Bis(hydroxymethyl)-2′-oxetanyl)-5-(2-iodo-1-vinyl)cytosine This compound is prepared in analogy to the procedure for Example 49, but substituting 1-([2′R, 3′R, 4′S]-3′,4′-bis(hydroxymethyl)-2′-oxetanyl)-5-iodocytosine for 1-([2′R, 3′R, 4′S]-3′,4′-bis(hydroxymethyl)-2′-oxetanyl)-5-iodouracil in Example 44.

Example 55

1-([2′R, 3′R, 4′S]-3′,4′-Bis(hydroxymethyl)-2′-oxetanyl)-5-(2-chloro-1-vinyl)cytosine This compound is prepared in analogy to the procedure for Example 50, but substituting 1-([2′R, 3′R, 4′S]-3′,4′-bis(hydroxymethyl)-2′-oxetanyl)-5-iodocytosine for 1-([2′R, 3′R, 4′S]-3′,4′-bis(hydroxymethyl)-2′-oxetanyl)-5-iodouracil in Example 44.

Example 56

1-([2′R, 3′R, 4′S]-3′,4′-Bis(hydroxymethyl)-2′-oxetanyl)-5-chlorocytosine

This compound is synthesized according to the procedure of Example 22 by substituting 4-N-acetyl-5-chlorocytosine for 4-N-acetylcytosine in the procedure of M. Saneyoshi, et al Chem Pharm Bull, 30, 2237-1982. This provides 2′,5′-bis-(O-(4″-chloro)benzoyl)-4-N-acetyl-5-chloro-3′-deoxycytidine, which is substituted for 2′,5′-bis-(O-(4″-chloro)benzoyl)-4-N-acetyl-3′-deoxycytidine in the procedures of Example 22.

Example 57

1-([2′R, 3′R, 4′S]-3′,4′-Bis(hydroxymethyl)-2′-oxetanyl)-5-(trifluoromethyl)cytosine This compound is synthesized according to the procedure of Example 22 by substituting 4-N-acetyl-5-(trifluoromethyl)cytosine for 4-N-acetylcytosine in the procedure of M. Saneyoshi, et al Chem Pharm Bull, 30, 2237-1982. This provides 2′,5′-bis-(O-(4″-chloro)benzoyl)-4-N-acetyl-5-(trifluoromethyl)-3′deoxycytidine, which is substituted for 2′,5′-bis-(O-(4″-chloro)benzoyl)-4-N-acetyl-3′-deoxycytidine in the procedures of Example 22.

Example 58

1-([2′R, 3′R, 4′S]-3′,4′-Bis(hydroxymethyl)-2′-oxetanyl)-5-fluorocytosine

This compound is synthesized according to the procedure of Example 22 by substituting 4-N-acetyl-5-fluorocytosine for 4-N-acetylcytosine in the procedure of M. Saneyoshi, et al Chem Pharm Bull, 30, 2237-1982. This provides 2′,5′-bis-(O-(4″-chloro)benzoyl)-4-N-acetyl-5-fluoro-3′-deoxycytidine, which is substituted for 2′,5′-bis-(O-(4″-chloro)benzoyl)-4-N-acetyl-3′-deoxycytidine in the procedures of Example 22.

Example 59

1-([2′R, 3′R, 4′S]-3′,4′-Bis(hydroxymethyl)-2′-oxetanyl)-5-methylcytosine

This compound is synthesized according to the procedure of Example 22 by substituting 4-N-acetyl-5-methylcytosine for 4-N-acetylcytosine in the procedure of M. Saneyoshi, et al Chem Pharm Bull, 30, 2237-1982. This provides 2′,5′-bis-(O-(4″-chloro)benzoyl)-4-N-acetyl-5-methyl-3′-deoxycytidine, which is substituted for 2′,5′-bis-(O-(4″-chloro)benzoyl)-4-N-acetyl-3′-deoxycytidine in the procedures of Example 22.

Example 60

1-([2′R, 3′R, 4′S]-3′,4′-Bis(hydroxymethyl)-2′-oxetanyl)-5-ethylcytosine

This compound is synthesized according to the procedure of Example 22 by substituting 4-N-acetyl-5-ethylcytosine for 4-N-acetylcytosine in the procedure of M. Saneyoshi, et al Chem Pharm Bull, 30, 2237-1982.

This provides 2',5'-bis-(O-(4''-chloro)benzoyl)-4-N-acetyl-5-ethyl-3'-deoxycytidine, which is substituted for 2',5'-bis-(O-(4''-chloro)benzoyl)-4-N-acetyl-3'-deoxycytidine in the procedures of Example 22.

Example 61

1-([2'R, 3'R, 4'S]-3',4'-Bis(hydroxymethyl)-2'-oxetanyl)-5-vinyluracil

To a stirred solution of 100 mg (0.428 mmol) of 1-([2'R, 3'R, 4'S]-3',4'-bis(hydroxymethyl)-2'-oxetanyl)-5-iodouracil, the product of Example 42, in 1.5 mL of DMF were added 159 mg (0.50 mmol) of vinyltributyl tin and 20 mg (0.029 mmol) of bis(triphenylphosphine)-palladium (II) chloride. The resulting mixture was heated under a $N_2$ atmosphere for 1 h at 60° C., cooled to room temperature, and then diluted with 75 mL of MeOH which had been saturated with hexane. The MeOH phase was then washed with 3×75 mL of hexane, filtered, and then concentrated under reduced pressure. Chromatography of the residue on silica gel with a 100:0 to 90:10/$CH_2Cl_2$:MeOH gradient afforded 40 mg (56%) of the title compound: $^1$H NMR (DMSO, TMS=0.00 ppm) δ3.2–3.8 (m, 5H), 4.48 (m, 1H), 4.94 (dd, 1H), 5.16 (dd, 1H), 5.46 (dd, 1H), 5.90 (dd, 1H), 6.30 (d, 1H), 6.41 (d, 1H), 8.73 (s, 1H), 11.45 (bs, 1H); FAB MS, m/z 255 $(M+H)^+$.

Example 62

1-([2'R, 4'S]-4'-(Hydroxymethyl)-2'-oxetanyl)-5-methyluracil

A solution of 356.5 mg (1 mmol) of 1-([2'R, 3'R, 4'S]-4'-((t-butyldimethysilyl)oxymethyl)-3'-hydroxymethyl-2'-oxetanyl)-5-methyluracil, the product of Step 7 of Example 21, is oxidized with 1.05 equivalents of the "Dess-Martin periodinane" according to the general procedure described by D. B. Dess and J. C. Martin, J. Org. Chem., 1983, 4165–4158. Chromatography of the crude reaction mixture on silica gel affords 1-([2'R, 3'R, 4'S]-4'-((t-butyldimethylsilyl)oxymethyl)-3'-formyl-2'-oxetanyl)-5methyluracil. A solution of 177 mg (0.5 mmol) of this aldehyde and 463 mg (0.5 mmol) of tris(-triphenylphosphine)rhodium(I) chloride in 5 mL of degassed acetonitrile is heated at 30°–150° C. in a sealed tube for 1 to 24 hours. Purification of the resulting reaction mixture on silica gel affords 1-([2'R, 4'S]-4'-((t-butyldimethysilyl)oxymethyl)-2'-oxetanyl)-5-methyluracil. A solution of 81 mg (0.25 mmol) of this silyl ether in 1 mL of THF is then treated with 65.4 mg (0.25 mmol) of tetrabutylammonium fluoride hydrate. After 6 h at room temperature, the reaction mixture is neutralized with 0.25 mmol of acetic acid and concentrated under reduced pressure. Chromatography of the residue on C18 Bondesil with a 100:0 to 50:50 gradient of water/MeOH affords the title compound.

Example 63

1-([2'R, 4'S]-4'-(Hydroxymethyl)-2'-oxetanyl)uracil

This compound is prepared in analogy to the procedure described for Example 62 by substituting 1-([2'R, 3'R, 4'S]-4'-((t-butyldimethysilyl)oxymethyl)-3'-hydroxymethyl-2'-oxetanyl)uracil, the product of Step 9 of Example 23, for 1-([2'R, 3'R, 4'S]-4'-((t-butyldimethysilyl)oxymethyl)-3'-hydroxymethyl-2'-oxetanyl)-5-methyluracil, the product of Step 7 of Example 21.

Example 64

1-([2'R, 4'S]-4'-(Hydroxymethyl)-2'-oxetanyl)cytosine

This compound is prepared in analogy to the procedure described for Example 62 by substituting 1-([2'R, 3'R, 4'S]-4'-((t-butyldimethysilyl)oxymethyl)-3'-hydroxymethyl-2'-oxetanyl)cytosine, the product of Step 8 of Example 22, for 1-([2'R, 3'R, 4'S]-4'-((t-butyldimethysilyl)oxymethyl)-3'-hydroxymethyl-2'-oxetanyl)-5-methyluracil, the product of Step 7 of Example 21.

Example 65

1-([2'R, 4'S]-3'-methylene-4'-hydroxymethyl)-2'-oxetanyl)-5-methyluracil
Step 1: 1-([2'R, 4'S]-3'-methylene-4'-((t-butyldimethysilyl)oxymethyl)-2'-oxetanyl)-5-methyluracil To a stirred solution of 435 mg (1 mmol) of 1-[2'R, 3'R, 4'S]-4'-((t-butyldimethylsilyl)oxymethyl)-3'-methanesulfonyloxymethyl-2'-oxetanyl-5-methyluracil, the product of Part a of Example 24, in 5 mL of acetonitrile is added 152 mg (1 mmol) of DBU, and the resulting mixture is heated to reflux for 1 to 24 hours. Concentration under reduced pressure and chromatography of the residue on silica gel affords the title compound.
Step 2: 1-([2'R, 4'S]-3'-methylene-4'-hydroxymethyl)-2'-oxetanyl)-5-methyluracil To a stirred solution of 1 mmol of the product from Step 1 of Example 65 in 10 mL of THF is added 1 mmol of tetra-n-butylammonium fluoride hydrate. After 6 h at room temperature, the reaction mixture is neutralized with 1 equivalent of acetic acid and then concentrated under reduced pressure. Chromatography of the residue on C18 Bondesil with a 100:0 to 50:50 gradient of water/MeOH affords the title compound.

Example 66

1-([2'R, 3'R, 4'R]-3'-Hydroxy-3',4'-bis(hydroxymethyl)-2'-oxetanyl)-5-methyluracil and 1-([2'R, 3'S, 4'R]-3'-Hydroxy-3',4'-bis(hydroxymethyl)-2'-oxetanyl)-5-methyluracil To a stirred solution of 1 mmol of 1-([2'R, 4'S]-3'-methylene-4'-((t-butyldimethysilyl)oxymethyl)-2'-oxetanyl)-5-methyluracil, the product of Step 1 of Example 65, in 5 mL of aqueous acetone is added 1 mmol of N-methylmorpholine-N-oxide and a catalytic amount of osmium tetroxide according to the general procedure of V. VanRheenen, R. C. Kelly, and D. Y. Cha, Tetraherdron Lett. 1976, 1973–1976. After 0.5 to 24 h at room temperature, the reaction mixture is diluted with ethyl acetate, washed with aqueous sodium bisulfite, dried over magnesium sulfate, and then concentrated under reduced pressure. The residue is then purified by chromatography on silica gel to afford the 4'-t-butyldimethylsilyl ether of the title compound. To a stirred solution of 0.5 mmol of this silyl ether in 2.5 mL of THF is added 0.5 mmol of tetra-n-butylammonium fluoride. After 6 h at room temperature, the reaction mixture is neutralized with acetic acid and then concentrated under reduced pressure. Chromatography of the residue on C18 Bondesil with a 100:0 to 50:50 gradient of water/MeOH affords the title compounds.

Example 67

1-([2'R, 3'R, 4'R]-3'-hydroxy-4'-hydroxymethyl)-2'-oxetanyl)-5-methyluracil and 1-([2'R, 3'S, 4'R]-3'-hydroxy-4'-hydroxymethyl)-2'-oxetanyl)-5-methyluracil To a stirred solution of 1 mmol of 1-([2'R, 3'R, 4'R]-3'-hydroxy-3',4'-bis(hydroxymethyl)-2'-oxetanyl)-5-methyluracil and 1-([2'R, 3'S, 4'R]-3'-hydroxy-3',4'-bis(- hydroxymethyl)-2'-oxetanyl)-5-methyluracil, the products of Example 66 in 10 mL of MeOH is added 1 mmol of a saturated solution of aqueous NaIO4. After 0.5 to 24 hours at room temperature, the reaction mixture is treated with excess sodium borohydride (1–20 equivalents) for 0.5 to 6 hours, filtered, and then concentrated under reduced pressure to remove MeOH. The resulting aqueous solution is then purified by chromatography on C18 Bondesil with a 100:0 to 50:50 gradient of water/MeOH to afford the title compounds.

Example 68

1-[2'R, 3'R, 4'S]-3',4'-Bis(hydroxymethyl)-2α-oxetanyl)-5-propynyluracil

Step 1: 1-[2'R, 3'R, 4'S]-4'-((t-Butyldimethylsilyl)oxymethyl)-3'-hydroxymethyl)2-oxetanyl)-5-propynyluracil To a stirred solution of 250 mg (0.53 mmol) of 1-[2'R, 3'R, 4'S]-4'-((t-Butyldimethylsilyl)oxymethyl)-2'-hydroxymethyl-2'-oxetanyl)-5-iodouracil, the product of Step 1 of Example 49, in 2 mL of DMF were added 150 µL (1.1 mmol) of triethylamine, 20 mg (0.11 mmol) of copper (I) iodide, 62 mg (0.11 mmol) of tetrakis (triphenylphosphine)palladium (0) and 150 mg (3.7 mmol) of propyne. After 20 hours at ambient temperature the mixture was concentrated under reduced pressure at 45°. The residue was dissolved in 50 mL CH2SO4 washed with 50 mL 5% NaHCO3, dried over MgSO4 and again concentrated under reduced pressure. Chromatography of the residue on silica gel with a 100:0 to 95:5 CH2Cl2/MeOH gradient afforded 112 mg (52%) of the title compound as an amorphous white solid: $^1$H NMR (CDCl3, TMS 0.00 ppm) δ0.13 (s, 3H), 0.15 (s, 3H), 0.93 (s, 9H), 2.04 (s, 3H), 2.77 (m, 1H), 3.63 (dd, 1H), 3.82 (dd, 1H), 3.96 (m, 2H), 4.60 (m, 1H), 6.14 (d, 1H), 8.28 (s, 1H), 8.52 (s, 1H); DCI NH3 MS, m/z 381 (M+H)+.

Step 2: 1-([2'R, 3'R, 4'S]-3',4'-Bis(hydroxymethyl)-2'-oxetanyl)-5-propynyluracil To a stirred solution of 105 mg (0.28 mmol) of 1-[2'R, 3'R, 4'S]-4'-((t-Butyldimethylsilyl)oxymethyl)-3'-hydroxymethyl-2'-oxetanyl)-5-propynyluracil, the product of Step 1 of Example 68, in 1 mL THF was added 96 mg (0.30 mmol) of tetra-n-butylammonium fluoride trihydrate. The mixture was stirred at ambient temperature for 5 hours and 16 µL of glacial acetic acid was added. The resultant solution was concentrated under reduced pressure. Chromatography of the residue on silica gel with a 95:5 to 9:1 CH2Cl2/MeOH gradient afforded 43 mg (59%) of the title compound as an amorphous white solid: $^1$H NMR (CD3OD, TMS 0.00 ppm) δ2.00 (s, 3H), 3.25 (m, 1H), 3.61 (dd, 1H), 3.78 (m, 2H), 3.83 (dd, 1H), 4.58 (m, 1H), 6.29 (d, 1H), 8.64 (s, 1H); FAB MS m/z: 267 (M+H)+; exact mass calculated for $C_{12}H_{15}N_2O_5$: 267.0981 (M+H)+, Found: 267.0975.

Example 69

1-([2'R, 3'R, 4'S]-3',4'-Bis(hydroxymethyl)-2'-oxetanyl)-5-ethynyluracil

Step 1: 1-[2'R, 3'R, 4'S]-4'-(t-Butyldimethylsilyl)oxymethyl)-3'-hydroxymethyl-2'-oxetanyl)-5-ethynyluracil To a stirred solution of 1.35 g (2.88 mmol) of the product of Step 1 of Example 49 in 17 ml of DMF were added 2.8 ml (8.1 mmol) of ethynyltributyltin and 310 mg (0.44 mmol) of bistriphenylphosphine palladium (II) chloride. The resulting mixture was heated under an nitrogen atmosphere at 60° C. for 6 hours. The reaction mixture was taken up in 150 ml of methanol saturated with hexane and washed with hexane (4×150 ml). The methanol phase was filtered and concentrated under reduced pressure. Chromatography of the residue on silica gel with a 99:1 to 97:3 CH2Cl2/MeOH gradient afforded 580 mg of the title compound as an amorphous white solid: $^1$H NMR (CDCl3, TMS=0.00 ppm) δ0.12 (s, 3H), 0.14 (s, 3H), 0.92 (s, 9H), 3.20 (s, 1H), 3.27 (m, 1H), 3.64 (dd, 1H), 3.85 (dd, 1H), 3.98 (m, 2H), 4.64 (m, 1H), 6.14 (d, 1H), 8.39 (s, 1H), 8.71 (s, 1H); DCI NH3 MS, m/z 384 (M+NH4)+.

Step 2: 1-[2'R, 3'R, 4'S]-3',4'-Bis(hydroxymethyl)-2-oxetanyl)-5-ethynyluracil

To a stirred solution of 540 mg (1.5 mmol) of the product of Step 1 of Example 69 in 10 ml of THF was added 512 mg (1.6 mmol) of tetra-n-butylammonium fluoride trihydrate. The mixture was stirred at ambient temperature for 3 hours and 138 µl of glacial acetic acid was added. The resultant solution was concentrated under reduced pressure. Chromatography of the residue on silica gel with a 95:5 to 9:1 CH2Cl2/MeOH gradient afforded 149 mg of the title compound as an amorphous white solid. The latter was digested with 1 ml of H2O for 2 hours at ambient temperature, filtered and washed with water to afford 72 mg of the title compound as white crystals: $^1$H NMR (CD3OD, TMS=0.00 ppm) δ3.27 (m, 1H), 3.55 (s, 1H), 3.61 (dd, 1H), 3.79 (m, 2H), 3.85 (dd, 1H), 4.61 (m, 1H), 6.29 (d, 1H), 8.81 (s, 1H); DCI NH3 MS, m/z 253 (M+H)+, m/z 270 (M+NH4)+.

The antiviral activity of the compounds of the invention can be determined by the following methods.

A. Evaluation of Compounds for Activity Against Herpes Simplex Virus Types 1 and Types 2

The challenge viruses were propagated and assayed in cells that were pregrown as monolayer cultures in plastic tissue culture flasks and 96-well plates, using cell culture media appropriate for the host cell cultures. The following viruses and host cell cultures were employed:

| Challenge Virus | Host Cell Type |
|---|---|
| Herpes simplex type 1 (HSV-1) strain E-377 | Continuous-passage African green monkey kidney (Vero) |
| Herpes simplex type 2 (HSV-2) strain MS | Continuous-passage African green monkey kidney (Vero) |

On the day of use, a weighed sample of each compound to be evaluated was dissolved and diluted in serial $10^{0.5}$ dilutions in the culture medium appropriate for each virus-host cell system.

CPE-Inhibition Assay Procedure

Mammalian cells were pregrown as monolayers in wells of COSTAR 96-well tissue culture plates using suitable cell culture media. Stock viruses were pretitered according to the method of Reed and Muench (Amer. J. Hyg. 27:493–497, 1938) and diluted in cell culture medium to yield 32 $CCID_{50}$ (cell culture infectious dose, 50%) units per 0.1 ml. Antiviral assays were designed to test seven concentrations of each compound, from cytotoxic to noncytotoxic levels, in triplicate against each of the challenge viruses in microtiter plate wells containing suitable cell monolayers. To each of the replicate cell cultures were added 0.1 ml of the test drug solution and 0.1 ml of virus suspension. Cell controls containing medium alone, virus controls containing medium and virus, and drug cytotoxicity controls containing medium and each drug concentration were run simultaneously with the test samples assayed in each experiment. The covered plates were incubated at 37° C. in a humidified atmosphere containing 5% $CO_2$ until maximum CPE (cytopathogenic effect) was observed in the untreated virus control cultures. The cell monolayers were examined microscopically for virus-induced CPE and for drug cytotoxicity.

Antiviral activity was determined by calculating the degree of inhibition of virus-induced CPE in drug-treated, virus-infected cell cultures by means of a virus rating (VR). The VR is a standard weighted measurement of antiviral activity taking into account both the degree of CPE inhibition and drug cytotoxicity, and is determined by a modification of the method of Ehrlich et al. (Ann. N.Y. Acad. Sci. 130: 5-16, 1965) as described below. CPE was graded for each individual culture in each microtiter plate well according to the following scale:

4 = 100% of the cells affected by virus;
3 = 75% of the cells affected by virus;
2 = 50% of the cells affected by virus;
1 = 25% of the cells affected by virus;
0 = No CPE; normal cell monolayer.

The VR was calculated as 0.1 of the sum of the numerical differences between the recorded CPE grade of each test well and that of the corresponding virus control in the culture plate. Numerical differences between the scores of test wells containing a drug concentration which was partially cytotoxic (p) and their corresponding virus controls were halved.

The minimum inhibitory drug concentration which reduced the cytopathogenic effect (CPE) by 50% ($MIC_{50}$) was calculated by using a regression analysis program for semilog curve fitting. A therapeutic index (TI) for each active compound for each susceptible virus was determined by dividing the minimum cytotoxic concentration of the test compound by the $MIC_{50}$. Test results are provided in Table 1.

Evaluation of Compounds for Activity Against Human Cytomegalovirus (HCMV)-Virus Yield Reduction Assay Human diploid embryonic lung (MRC5) cells were grown in 35 mm wells of 6-well tissue culture plates. Subconfluent cell monolayers were rinsed with phosphate-buffered saline (PBS) and were exposed to 0.5 ml/well of HCMV (strain AD169) suspension for 1.5 hours at 37° C. The virus suspension was diluted in MEM+2% fetal bovine serum (FBS) to yield a multipicity of infection (MOI) of approximately 0.1 plaque forming units (PFU)/cell. Following the virus adsorption period, the inocula were removed and infected cell layers were rinsed with PBS. Aliquiots (2.0 ml) of each test drug concentration (dissolved in MEM supplemented with 2% FBS) were dispensed into triplicate cell cultures: two virus-infected cultures and one uninfected cytotoxicity control culture (exposed to medium without virus for 1.5 hours). Untreated virus-infected control cultures and untreated, uninfected cell control cultures were fed with medium alone. The culture plates were incubated at 37° C. in a humidified atmosphere of 2% $CO_2$ in air.

All cell culture fluids were replaced with fresh drug and medium 48 hours postinfection (p.i.).

On Day 6 p.i., the cell layers were examined microscopically for cytopathogenic effect (CPE) and drug cytotoxicity. The test and virus control cultures were then harvested by subjecting the cell layers to one cycle of freeze-thawing. The cellular material was scraped into the ambient medium and the contents from replicate cultures were pooled, dispensed into cryotubes and stored at −135° C.

Drug cytotoxicity was determined quantitatively by a method based on the reduction of the tetrazolium salt, 3-(4,5-dimethyl-thiazol-2-yl)-2,5-diphenyl tetrazolium bromide (MTT) by mitochondrial enzymes of viable host cells to MTT formazan (T. Mosmann, 1983). Drug cytotoxicity controls and cell controls were treated with MTT (dissolved in culture medium) followed by 20% SDS (in 0.02N HCl) to dissolve the crystals of MTT formazan. The blue color of the MTT formazan was measured spectrophotometrically at 570 nm. Drug cytotoxicity was determined by comparing the absorbance (O.D.) of each drug cytotoxicity control with the mean O.D. of the cell control cultures and expressed as percent of control.

The harvested test and virus control samples were thawed and the infectious virus yield was determined by plaque assay in MRC5 cells grown in 12-well cluster plates. Inhibition of HCMV replication by each test compound was determined by comparing the progeny virus yields in the drug-treated cultures with the progeny virus yield in the untreated, virus-infected control cultures. Test results are provided in Table 2.

C. Evaluation of Compounds for Activity Against Varicella-Zoster Virus (VZV)-Plaque Reduction Assay The compounds of the invention were evaluated for selective activity against varicella zoster virus (VCV) utilizing a plaque reduction assay procedure. The challenge virus was a clinical isolate designated DM625, obtained from Dr. Richard Whitley of the University of Alabama Hospitals, Birmingham, Ala. The virus had been passaged and titrated in cultures of human foreskin fibroblasts (HFF).

For the plaque reduction assay, sixth to twelfth passage human foreskin fibroblasts were seeded in wells of 12-well tissue culture plates and incubated at 37° C. in a humidified atmosphere containing 2% $CO_2$ in air. Subconfluent HFF were rinsed with MEM and exposed to 0.5 ml/well of a suspension of VZV diluted in MEM+2% FBS for 2 hours at 37° C. Following the virus adsorption period, the inocula were removed and the infected cell layers were rinsed with MEM. Triplicate VZV-infected cell culture wells were treated with 1.0 ml of each concentration of test compound (in MEM+2% FBS). Six untreated virus-infected cell cultures and triplicate untreated uninfected cell cultures were fed with 1.0 ml of MEM+2% FBS to serve as controls. Wells containing uninfected HFF were treated with each concentration of test compound to monitor the test compound cytotoxicity. The 12-well plates were incubated at 37° C. in the $CO_2$ incubator. At 48 hours post-virus infection (p.i.), fluids in all plate wells were replaced with fresh test compound and/or culture medium.

Six days p.i., the VZV plaques were counted (unstained, low magnification). The effect of each concentration of test compound on plaque formation was determined by comparing the mean number of plaques in the replicate test compound-treated cultures with the mean plaque counts of the untreated virus control cultures.

The test compound cytotoxicity control cultures were examined microscopically for gross morphologic changes, then treated with MTT and 30% SDS. The blue color of the MTT formazan was measured spectrophotometrically at 570 nm. Test compound cytotoxicity was determined by comparing the absorbance (O.D.) of each test compound control with the mean O.D. of the cell control cultures and expressed as percent of control.

Test results are provided in Table 3. The $MIC_{50}$ value is the minimum concentration of test Compound required to inhibit plaque formation by 50%.

D. Alternate Method For Evaluation Of Compounds For Activity Against Herpes Simplex Virus Type 1

Neutral Red Dye Uptake Assay For Determining In Vitro Antiviral Activity

Vero cell monolayers were harvested by trypsinization. The number of viable cells per ml. was determined by staining an aliquot with trypan blue and counting in a hemocytometer. Cell densities were adjusted in growth medium to contain $4 \times 10^5$ cells/mi. 96-well sterile tissue culture plates were seeded with 100 μl/well of the adjusted cell suspensions, i.e., $4 \times 10^4$ cells/well. Seeded plates were incubated overnight at 37° C. with $CO_2$.

After overnight incubation, monolayers were approximately confluent. The growth medium was removed and the monolayers in each cell were infected with 100 μl of virus diluted in maintenance medium to produce approximately 90% cytopathogenic effect (CPE) after 2 to 3 days incubation. The virus was allowed to adsorb for 1 hour at 37° C. with 4 to 6% CO2. Controls for cell growth were overlayed with virus-free maintenance medium. The maintenance medium containing residual virus was removed.

The test compounds were dissolved and/or diluted in maintenance medium to the concentration desired for testing and were added to the wells of the plate. Aliquots (100 μl ) of each concentration were added to wells in replicate (duplicate or triplicate). Controls for virus activity were overlayed with drug-free maintenance medium. Replicate wells containing only maintenance medium served as controls for background absorbance levels.

The plates were incubated at 37° C. with $CO_2$ until approximately 90% CPE was observed in the virus infected control cells (usually 2 to 3 days). After incubation, the medium was removed from all the wells. 100 μl of neutral red solution was added to each well and the plate was incubated at 37° C. without $CO_2$ for 2 hours. After the 2 hour incubation, the excess neutral red solution was removed. The plates were washed with 100 μl/well of PBS, pH 7.2 and then the PBS was removed.

The neutral red stain taken up by the viable cells was extracted by adding 100 μl/well of acidified methanol, pH 1.0. (The acidified methanol fixed the cells to the well). The plate was allowed to stand at room temperature for at least 15 minutes to allow for maximum extraction. The amount of neutral red stain extracted into the methanol was quantified by determining the absorbance at a wavelength of 540 nm.

Reagents

1% aqueous Neutral Red Salt was prepared by mixing 1 gram of neutral red salt in 100 ml of distilled water.

Neutral Red Staining Solution was prepared by mixing 100 ml of 1X PBS, pH 7.2, 1 drop of 0.5% aqueous phenol red, 2-3 drops of 2N HCl (until solution turns yellow-orange) and 0.66 ml of 1% aqueous neutral red.

Acidified methanol was prepared by mixing 8 drops of 2N HCl in 100 ml of methanol.

10X Phosphate Buffered Saline (PBS), pH 7.2, was prepared by mixing 12.36 grams of Na2HPO4 (anhydrous), 1.80 grams of NaH2PO4 (monohydrate) in distilled water, adjusting the pH to 7.2 and bringing the final volume to 1 liter.

Results

The percent CPE in virus controls was determined by the following formula:

$$\frac{Abs_{540} \text{ cell controls} - Abs_{540} \text{ virus controls}}{Abs_{540} \text{ cell controls}} \times 100$$

The percent CPE in cells infected with virus and treated with the test compound was determined by the following formula:

$$\frac{Abs_{540} \text{ cell controls} - Abs_{540} \text{ test compound}}{Abs_{540} \text{ cell controls}} \times 100$$

A plot was made of the percent CPE versus concentration of the test compound. The concentration of test compound at which 50% CPE would be observed is read from the dose-response curve and is the $MIC_{50}$ (μg/ml). The concentration of test compound which is toxic to 50% of control cells is shown as the $TD_{50}$. Test results are provided in Table 4.

E. Alternate Method For Evaluation of Compounds For Activity Against Herpes Simplex Virus Types I and II CPE Inhibition Assay Procedure (MTT)

Vero cells were pregrown as monolayers in wells of COSTAR 96-well tissue culture plates using suitable cell culture media. Stock viruses were pretitered according to the method of Reed and Muench (Amer. J. Hyg. 27 493 (1938)) and diluted in cell culture medium to yield 32 $CCID_{50}$ (cell culture infectious dose, 50%) units per 0.1 mL. Antiviral assays were designed to test six concentrations of each compound, from cytotoxic to noncytotoxic levels, in triplicate against each of the challenge viruses in microtiter plate wells containing cell monolayers. To each of the replicate cell cultures were added 0.1 mL of the test-compound solution and 0.1 mL of virus suspension. Two compounds were evaluated per plate. The following controls were included:

(1) Cell controls containing cells+medium;
(2) Untreated, virus-infected cell controls;
(3) Test-compound cytotoxicity controls containing uninfected, test-compound treated cells;
(4) Test-compound color controls—test-compound-+medium (no cells); and
(5) Reagent (experiment medium) controls—medium only (no cells).

The covered plates were incubated at 37° C. in a humidified atmosphere containing 2% CO2. When cytopathogenic effect (CPE) in untreated virus control wells reached 100%, 20 μL of 3-(4,5-dimethyl-thiazol-2-yl)-2,5-diphenyl tetrazolium bromide (MTT) (dissolved in PBS at 5 mg/mL) was pipetted into each of the plate wells. The plates were incubated at 37° C. for six hours; then 40 μL of 30% SDS (in 0.02N HCl) was added to each well. After overnight incubation at 37° C., the blue color or the MTT formazan was measured spectrophotometrically at 570 nm. The optical density (OD) value of each culture is a function of the amount of formazan produced which is proportional to the number of viable cells. A computer program was utilized to calculate the percent (CPE) reciprocal of % CPE reduction) of the virus-infected wells and % cell viability of the uninfected test-compound control wells.

Test results are provided in Table 5. The $IC_{50}$ value is the minimum test-compound concentration (μg/mL) that inhibited CPE by 50% calculated by using a regression analysis program for semilog curve fitting. The $TC_{25}$ value is the minimum test-compound concentration (μg/mL) that reduced cell viability by 25%.

TABLE 1

Antiviral Activity of Compounds of Formula I Against Herpes Simplex

| Challenge Virus: | Herpes Simplex Type 1 (E-377) | | | | Herpes Simplex Type 2 (MS) | | | |
|---|---|---|---|---|---|---|---|---|
| Host Cell Type: | Vero | | | | Vero | | | |
| Compound of Example No. | $VR^1$ | $ID50^2$ | $MTC^3$ | $TI^4$ | VR | ID50 | MTC | TI |
| 21 | 5.9 | 0.2 | 320 | 1552 | 2.9 | 44.3 | >320 | >7.2 |
| 22 | 2.65 | 0.8 | 10 | 13.1 | 1.95 | 1.0 | 10 | 9.7 |
| 23 | 0.6 | 306.7 | 320 | 1.0 | 0.5 | | 320 | |

[1] VR = Virus Rating: A measurement of selective antiviral activity which takes into account the degree of virus-induced cytopathogenic effects (CPE) and the degree of cytotoxicity produced by the test compound, determined by a modification of the method of Ehrlich et al. (Ann. N.Y. Acad. Sci. 130: 5–16, 1965). A VR |1.0 indicates definite (+) antiviral activity, a VR of 0.5–0.9 indicates marginal to moderate antiviral activity, and a VR < 0.5 usually indicates no significant antiviral activity.
[2] ID50 = The minimum drug concentration (ug/ml) that inhibited the CPE by 50%, calculated by using a regression analysis program for semilog curve fitting.
[3] MTC = The minimum drug concentration (ug/ml) causing any cytotoxicity.
[4] TI = Therapeutic Index, calculated by dividing the minimum cytotoxic drug concentration by the ID50.

The results indicate that the compounds are active against HSV-1 and HSV-2.

TABLE 2

Antiviral Activity of Compounds of Formula I Against Human Cytomegalovirus (HCMV) In MRC5 Cells

| Compound | Drug Conc. (μg/ml) | HCMV yield (log10 PFU/ml) | HCMV yield reduction (log10 PFU/ml) | MTT assay Percent of control |
|---|---|---|---|---|
| Ex. 22 | 0.032 | 3.8 | 0.8 | |
| | 0.1 | 3.1 | 1.4 | |
| | 0.32 | 2.6 | 1.9 | 84 |
| | 1.0 | 0.4 | 4.1 | 81 |
| | 3.2 | <0.1 | >4.4 | 77 |
| | 10 | <0.1 | >4.4 | 78 |
| Ex. 23 | 3.2 | 4.7 | 0.2 | |
| | 10 | 4.5 | 0.4 | 100 |
| | 32 | 4.4 | 0.5 | 100 |
| | 100 | 4.0 | 0.9 | 98 |
| | 320 | 3.0 | 1.9 | 100 |

The results indicate that the compound is active against HCMV.

TABLE 3

Antiviral Activity of Compounds of Formula I Against Varicalla-Zoster Virus (VZV)

| Compound | Drug Conc. (μM) | Plaque Reduction (%) | MTT assay (Percent of control) | MIC50 (μg/mL) |
|---|---|---|---|---|
| Ex. 21 | 0.032 | 16 | | 0.09 |
| | 0.1 | 55 | 93 | |
| | 0.32 | 97 | 84 | |
| | 1.0 | 100 | 87 | |
| | 3.2 | 100 | 87 | |
| Ex. 22 | 0.032 | 29 | | 0.07 |
| | 0.1 | 86 | 88 | |
| | 0.32 | 100 | 81 | |
| | 1.0 | 100 | 77 | |
| | 3.2 | 100 | 76 | |
| Ex. 23 | 1.0 | 22 | | 19.4 |
| | 3.2 | 22 | 82 | |
| | 10 | 34 | 84 | |

TABLE 3-continued

Antiviral Activity of Compounds of Formula I Against Varicalla-Zoster Virus (VZV)

| Compound | Drug Conc. (μM) | Plaque Reduction (%) | MTT assay (Percent of control) | MIC50 (μg/mL) |
|---|---|---|---|---|
| | 32 | 84 | 87 | |
| | 100 | 100 | 88 | |
| | 320 | 100 | 82 | |
| Ex. 42 | 0.032 | 7 | | 0.1 |
| | 0.1 | 2 | | |
| | 0.32 | 54 | | |
| | 1.0 | 76 | 93 | |
| | 3.2 | 98 | 94 | |
| | 10 | 99 | 80 | |
| | 32 | 100 | 88 | |
| | 100 | 100 | 82 | |
| | 320 | 99.6 | 79 | |
| | 1000 | 100 | 68 | |
| Ex. 43 | 0.032 | 1 | 100 | 0.17 |
| | 0.1 | 12 | 100 | |
| | 0.32 | 41 | 96 | |
| | 1.0 | 75 | 100 | |
| | 3.2 | 98 | 93 | |
| | 10 | 99 | 99 | |
| | 32 | 99 | 93 | |
| | 100 | 100 | 100 | |
| | 320 | 100 | 88 | |
| | 1000 | 100 | 82 | |
| Ex. 44 | 0.0001 | 3 | 99 | 0.0032 |
| | 0.00032 | 6 | 98 | |
| | 0.001 | 4 | 93 | |
| | 0.0032 | 16 | 100 | |
| | 0.01 | 54 | 97 | |
| | 0.032 | 97 | 94 | |
| | 0.1 | 98 | 92 | |
| | 0.32 | 99 | 92 | |
| | 1.0 | 99 | 100 | |
| | 3.2 | 100 | 100 | |
| Ex. 49 | 0.0032 | 18 | | 0.01 |
| | 0.01 | 49 | | |
| | 0.032 | 97 | | |
| | 0.1 | 98 | 100 | |
| | 0.32 | 98 | 100 | |
| | 1.0 | 99 | 100 | |
| Ex. 50 | 0.0032 | 7 | | 0.004 |
| | 0.01 | 45 | | |
| | 0.032 | 90 | | |
| | 0.1 | 99 | 100 | |
| | 0.32 | 98 | 100 | |
| | 1.0 | 99 | 100 | |
| Ex. 68 | 0.032 | 3 | 100 | 0.045 |
| | 0.1 | 38 | 100 | |
| | 0.32 | 92 | 100 | |
| | 1.0 | 99 | 98 | |
| | 3.2 | 100 | 100 | |

The results indicate that the compounds are active against Varicella-Zoster virus.

TABLE 4

Antiviral Activity of Compounds of Formula I Against Herpes Simplex 1

| Compound | MIC$_{50}$ (μg/ml) | TD$_{50}$ (μg/ml) |
|---|---|---|
| Ex. 44 | 0.09 | >1000 |
| Ex. 48 | 0.06 | 350 |
| Ex. 61 | 0.02 | >1000 |

The results indicate that the compounds are active against Herpes Simplex 1.

TABLE 5

Antiviral Activity of Compounds of Formula I Against Herpes Simplex

| Compound of Example No. | Challenge Virus | IC$_{50}$* (ug/mL) | TC$_{25}$* (ug/mL) |
|---|---|---|---|
| 42 | HSV-1 (E-377) | 0.05 | >354 |
|    | HSV-2 (MS)    | 35.3 | >354 |
| 43 | HSV-1 (E-377) | 0.7 | 18.4 |
|    | HSV-2 (MS)    | 141.0 | >307 |
| 44 | HSV-1 (E-377) | 0.072 | 289 |
| 49 | HSV-1 (E-377) | 0.67 | >380 |
| 50 | HSV-1 (E-377) | 0.74 | >289 |
| 61 | HSV-2 (MS)    | 6.3 | ≥254 |

The results indicate that the compounds are active against HSV-1 and HSV-2.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of esters. Examples of such esters include a hydroxyl-substituted compound of the invention which has been acylated with a blocked or unblocked amino acid residue, a phosphate function or a hemisuccinate residue. Such esters also include hydroxyl-substituted compounds of the invention wherein the hydroxyl group is acylated to provide esters such as acetate, propionate, benzoate and the like. Other esters include the compounds of the invention wherein a carboxylic acid group has been esterified to provide esters which include, but are not limited to, methyl, ethyl, benzyl and the like. The preparation of esters of the compounds of the present invention is carried out by reacting a hydroxyl-substituted compound of the invention with an activated acyl, amino acyl, phosphoryl or hemisuccinyl derivative. Compounds which are esters of carboxylic acid group containing compounds of the invention are prepared by methods known in the art.

The novel compounds of the present invention possess antiviral activity and are useful for treating or preventing diseases related to susceptible viruses (in particular, herpes viruses, such as herpes simplex types 1 and 2, cytomegalovirus and varicella-zoster) in humans or other mammals. The compounds of the present invention are also expected to be useful for treating or preventing diseases related to hepatitis viruses, such as hepatitis A, hepatitis B and non-A, non-B hepatitis, papilloma virus, influenza viruses, rhinovirus, respiratory syncytial virus, Epstein-Barr virus and HIV in humans or other mammals.

Total daily dose administered to a host in single or divided doses may be in amounts, for example, from 0.1 to 2000 mg/kg body weight daily and more usually 1.0 to 500 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of ointments, creams or ophthalmically acceptable solutions, suspensions, emulsions, ointments and solid inserts. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono -or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, ganciclovir, dideoxycytidine (DDC), dideoxyinosine (DDI), BCH-189, AzdU, carbovir, DDA, D4C, D4T, DP-AZT, FLT (fluorothymidine), BCH-189, 5-halo-3'-thia-dideoxycytidine, PMEA, zidovudine (AZT) and the like), non-nucleoside reverse transcriptase inhibitors (for example, R82193, L-697,661, BI-RG-587 (nevirapine), HEPT compounds, L,697,639, R82150, U-87201E and the like), TAT inhibitors (for example, RO-24-7429 and the like), HIV protease inhibitors, trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C$_{87}$, foscarnet, BW256U87, BW348U87, BV ara-U, CMV triclonal antibodies, FIAC, HOE-602, HPMPC, MSL-109, TI-23, trifluridine, vidarabine, famciclovir, penciclovir, acyclovir, castanospermine, rCD4/CD4-IgG, CD4-PE40, butyl-DNJ, hypericin, oxamyristic acid, dextran sulfate and pentosan polysulfate. Immunomodulators that can be administered in combination with a compound of the present invention include bropirimine, Ampligen, anti-human alpha interferon antibody, colony stimulating factor, CL246, 738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis facator, beta interferon, gamma interferon, interleukin-4, autologous CD8+ infusion, alpha interferon immunoglobulin, anti-Leu-3A, autovaccination, biostimulation, extracorporeal photophoresis, FK-565, FK-506, G-CSF, GM-CSF, hyperthermia, isopinosine, IVIG, passive immunotherapy and polio vaccine hyperimmunization. Other antiinfective agents that can be administered in combination with a compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-Immunogen, p24 (recombinant), Vax-Syn HIV-1 (p24) can be used in combination with a compound of the present invention.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A process for the preparation of a compound of the formula:

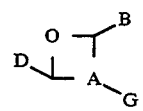

wherein B is

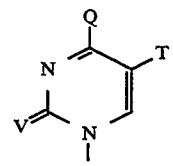

wherein

V is O or S;

Q is (i) —OH or (ii) —NH; and

T is (i) hydrogen, (ii) $C_1$ to $C_{10}$ alkyl, (iii) 2-haloethyl, (iv) halomethyl, (v) difluoromethyl, (vi) trifluoromethyl, (vii) halogen, (viii) vinyl, (ix) 2-halovinyl or (x) alkynyl;

A is CH and D and G are —CH$_2$OH; or a pharmaceutically acceptable salt or ester thereof, comprising the step wherein a compound of the formula:

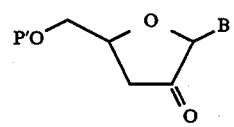

wherein P' is a hydroxyl protecting group and B is defined as above is transformed by ring contraction to a compound of the formula:

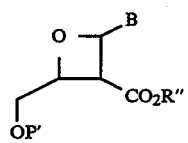

wherein B is defined as above, P' is a hydroxyl protecting group and R" is loweralkyl.

2. The process of claim 1 wherein the ring contraction is accomplished via a diazoketone intermediate of the formula:

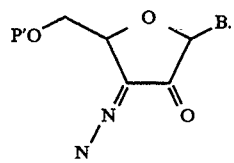

3. A process for the preparation of a compound of the formula:

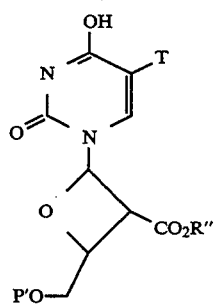

wherein T is (i) hydrogen, (ii) $C_1$ to $C_{10}$ alkyl, (iii) 2-haloethyl, (iv) halomethyl, (v) difluoromethyl, (vi) trifluoromethyl, (vii) halogen, (viii) vinyl, (ix) 2-halovinyl or (x) alkynyl;

P' is a hydroxyl protecting group and R" is loweralkyl comprising ring contraction of a compound of the formula:

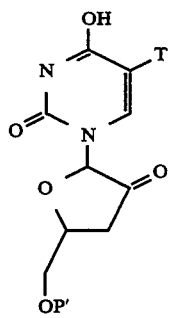

wherein T and P' are defined as above.

4. The process of claim 3 wherein the ring contraction is accomplished via a diazoketone intermediate of the formula:

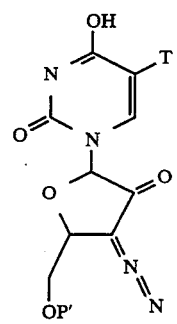

wherein T and P' are as defined therein.

5. A process for the preparation of a compound of the formula:

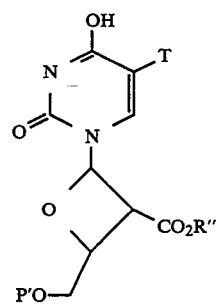

wherein T is hydrogen or $C_1$ to $C_{10}$ alkyl, P' is a hydroxyl protecting group and R" is loweralkyl comprising ring contraction of a compound of the formula:

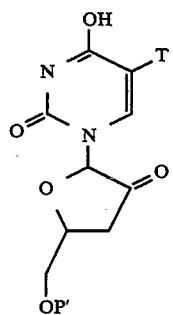

wherein T and P' are defined as above.

6. The process of claim 5 wherein the ring contraction is accomplished via a diazoketone intermediate of the formula:

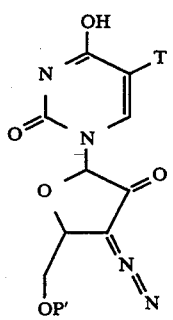

wherein T and P' are as defined therein.

* * * * *